(12) United States Patent
Ho et al.

(10) Patent No.: US 12,134,776 B2
(45) Date of Patent: Nov. 5, 2024

(54) DEVELOPMENT OF OPTIMIZED RECOMBINANT EXPRESSION CONSTRUCT

(71) Applicant: G&P BIOSCIENCE CO., LTD., Seoul (KR)

(72) Inventors: Seong Hyun Ho, Seoul (KR); Su Jin Park, Seoul (KR)

(73) Assignee: G&P BIOSCIENCE CO., LTD., Seoul (KR)

( * ) Notice: Subject to any disclaimer, the term of this patent is extended or adjusted under 35 U.S.C. 154(b) by 90 days.

(21) Appl. No.: 17/495,233

(22) Filed: Oct. 6, 2021

(65) Prior Publication Data

US 2023/0212603 A1 Jul. 6, 2023

(51) Int. Cl.
| | | |
|---|---|---|
| *C12N 15/00* | (2006.01) | |
| *A61K 48/00* | (2006.01) | |
| *C07K 14/005* | (2006.01) | |
| *C07K 14/475* | (2006.01) | |
| *C12N 7/00* | (2006.01) | |
| *C12N 15/85* | (2006.01) | |

(52) U.S. Cl.
CPC .......... *C12N 15/85* (2013.01); *A61K 48/0066* (2013.01); *C07K 14/005* (2013.01); *C07K 14/4753* (2013.01); *C12N 7/00* (2013.01); *C12N 2710/16143* (2013.01); *C12N 2800/107* (2013.01); *C12N 2830/34* (2013.01)

(58) Field of Classification Search
CPC ................. C12N 15/85; C12N 7/00; C12N 2710/16143; C12N 2800/107; C12N 2830/34; A61K 48/0066; C07K 14/005; C07K 14/4753
See application file for complete search history.

(56) References Cited

U.S. PATENT DOCUMENTS

| | | | | |
|---|---|---|---|---|
| 2003/0166890 A1* | 9/2003 | Crombie | ................ | C12N 15/85 536/23.1 |
| 2005/0079581 A1* | 4/2005 | Kim | .................. | C07K 14/4753 435/325 |
| 2008/0199493 A1* | 8/2008 | Picker | ..................... | A61P 37/04 435/320.1 |
| 2014/0179005 A1* | 6/2014 | Jantz | ...................... | C12N 9/003 435/462 |
| 2015/0246086 A1* | 9/2015 | Zhang | ................ | A61K 35/763 424/93.2 |

FOREIGN PATENT DOCUMENTS

KR 100562824 3/2006

OTHER PUBLICATIONS

Zhu et al (Virology Journal 2011, vol. 8, No. 344: pp. 1-5). Zhu et al uses pVAX1 vector to make expression cassettes expressing heterogenous genes (See Title, Abstract, entire article). (Year: 2011).*
The de Sousa Dissertation (Jun. 2011). (Year: 2011).*
Taherkhani et al (Jundishapur J Microbiol 2014 vol. 7, No. 11, published online Nov. 1, 2014: pp. 1-8). (Year: 2014).*
Madeira et al (Journal of Biomedicine and Biotechnology vol. 2010, pp. 1-10). (Year: 2010).*

* cited by examiner

*Primary Examiner* — Catherine S Hibbert
(74) *Attorney, Agent, or Firm* — DUANE MORRIS LLP; Gregory M. Lefkowitz; Brandon A. Chan

(57) ABSTRACT

The present disclosure relates to development of a eukaryotic cell expression vector satisfying optimized conditions for gene therapies and DNA vaccines. As a result of replacing the full HCMV regulatory and transcribed region including the immediate early (IE) gene intron A of the HCMV Towne strain and the same region of various HCMV strains at the pVAX1 promoter region and comparing the difference in gene expression efficiency for the different HCMV strains, the eukaryotic cell expression vector of the present disclosure could increase the expression of various genes by about 50-150% as compared to the HCMV Towne strain. Through this, pHP3 was developed as a vector exhibiting high expression in eukaryotic cells, and it can be usefully used for gene therapies or DNA vaccines.

7 Claims, 8 Drawing Sheets

Specification includes a Sequence Listing.

DEVELOPMENT OF OPTIMIZED RECOMBINANT EXPRESSION CONSTRUCT

SEQUENCE LISTING

The instant application contains a Sequence Listing, which has been submitted electronically in ASCII format and is hereby incorporated by reference in its entirety. Said ASCII text file, created on Dec. 20, 2021, is named G1035-20801_RevisedSequenceListing and is 62,338 bytes in size.

BACKGROUND

1. Field

The present disclosure relates to development of an expression construct having high expression efficiency in gene therapies and/or DNA vaccines, more particularly to a recombinant expression construct for expressing a transgene prepared by inserting the full HCMV IE regulatory and transcribed region of an optimized HCMV strain into a pVAX1 vector.

2. Description of the Related Art

All gene therapies are classified into viral or non-viral depending on the type of a vector that delivers a therapeutic gene. Among them, plasmid DNAs exhibiting high safety and adenoviruses or adeno-associated viruses with superior expression efficiency are used the most frequently. Because a plasmid DNA-based gene therapy has low expression efficiency, researches are actively being conducted in various directions to improve the expression efficiency of therapeutic genes.

In general, three methods are being researched to increase the expression efficiency of therapeutic genes. They are: improvement of expression vectors through, e.g., combination with promoters; improvement of genes optimized for specific diseases; and improvement of in-vivo delivery efficiency. Among them, the present disclosure aims at developing a vector exhibiting optimized expression efficiency in eukaryotic cells by comparing and screening gene-expressing promoters.

The HCMV promoter is one of the most powerful promoters. There are various HCMV strains. Towne, AD169, etc. are representative strains. The base sequence of the major promoter of the HCMV immediate early (IE) gene is similar with little difference among the strains, but it shows difference in the base sequence of the full HCMV IE regulatory and transcribed region including intron A among different HCMV strains. Chapman et al. have previously reported the expression efficiency is increased in the gp120 and gp160 genes when the intron A of the HCMV Towne strain is included in a promoter (full HCMV regulatory and transcribed region). However, the difference in gene expression depending on the promoter for different HCMV strains is not known.

The pVAX1 vector, which is currently used in many clinical trials, uses the major promoter of the HCMV IE gene of the AD169 strain. However, it does not show high expression efficiency although it has excellent safety in clinical trials. Therefore, many researchers are studying to increase the expression efficiency of this vector.

The above information disclosed in this Background section is only for enhancing the understanding of the background of the present disclosure, and therefore it may contain information that does not form the prior art that is already known to those having ordinary knowledge in the art.

REFERENCES OF THE RELATED ART

Patent Documents

Korean Patent Registration No. 10-0562824.

SUMMARY

The inventors of the present disclosure have made consistent efforts to develop a vector exhibiting high expression efficiency in eukaryotic cells, which is suitable for use in gene therapies or DNA vaccines. As a result, they have identified that gene expression efficiency is increased remarkably when the full HCMV IE regulatory and transcribed region of the HCMV 3157 strain is used as compared to when the full HCMV IE regulatory and transcribed regions derived from other strains are used, and have completed the present disclosure.

Accordingly, the present disclosure is directed to providing a recombinant expression construct.

The present disclosure is also directed to providing a recombinant expression construct including a sequence having 90% or higher homology to the full HCMV IE regulatory and transcribed region sequence of the HCMV 3157 strain.

The present disclosure is also directed to providing a recombinant expression construct for expressing a transgene.

The present disclosure is also directed to providing a host cell to which the recombinant expression construct or the recombinant expression construct for expressing a transgene has been transduced.

The present disclosure is also directed to providing a method for preparing the recombinant expression construct or the recombinant expression construct for expressing a transgene.

The present disclosure is also directed to providing a therapeutic use (use in therapy) of the recombinant expression construct for expressing a transgene.

The present disclosure is also directed to providing a method for expressing a transgene, which includes a step of administering a therapeutically effective amount of the recombinant expression construct for expressing a transgene to a subject in need thereof.

The present disclosure is also directed to providing a pharmaceutical composition containing a pharmaceutically effective amount of the recombinant expression construct for expressing a transgene and a pharmaceutically acceptable carrier.

Other purposes and advantages of the present disclosure will become apparent by the following detailed description, claims and attached drawings.

In an aspect of the present disclosure, the present disclosure provides a recombinant expression construct.

In the present specification, the term "vector" or "construct" refers to a construct capable of inserting a nucleic acid or a gene. Specifically, it includes a vector that can insert a nucleic acid sequence for introduction into a cell which is capable of replicating a nucleic acid sequence. The nucleic acid sequence may be exogenous or heterologous. The nucleic acid sequence may be a transgene. Examples of the construct include a plasmid, a cosmid and a virus (e.g., AAV), although not being limited thereto. Those skilled in the art can construct the vector or construct using standard recombinant techniques (Maniatis, et al., *Molecular Cloning*, A Laboratory Manual, Cold Spring Harbor Press, Cold Spring Harbor, N.Y., 1988; Ausubel et al., In: *Current Protocols in Molecular Biology*, John, Wiley & Sons, Inc, N Y, 1994; etc.).

In the present specification, the term "expression vector" or "expression construct" refers to a vector or a construct including a nucleotide sequence which encodes at least a portion of a transcribed gene product. In some cases, RNA molecules are translated to proteins, polypeptides or peptides thereafter. The expression construct may contain various regulatory regions. In addition to the regulatory regions that regulate transcription and translation, nucleotide sequences providing other functions may also be included in the expression vector. The regulatory elements may include enhancer, promoter, exon, intron, splicing donor and acceptor sequences, etc. In addition, the regulatory element may include a sequence for terminating transcription (e.g., poly A, etc.), a sequence for stably expressing a transgene (e.g., WPRE sequence, etc.) or a sequence for reducing transgene-specific immunity (e.g., miRNA target sequence, etc.).

In the present specification, the term "operationally linked" or "operably linked" means that DNA sequences being linked are arranged contiguously to perform desired functions. For example, a specific promoter which helps the initiation of the transcription of a coding sequence (e.g., transgene) may be operationally linked to the coding region. There may be intervening residues between the promoter and the coding region as long as this functional relationship is maintained.

In the present specification, the term "full HCMV IE regulatory and transcribed region" refers to a structure which includes a regulatory and transcribed region such as an enhancer, a promoter, intron A, etc. A "major HCMV IE promoter" refers to a structure wherein non-essential elements such as intron A, etc. are missing from the "full HCMV IE regulatory and transcribed region".

In a specific exemplary embodiment of the present disclosure, the full HCMV IE regulatory and transcribed region sequence of the HCMV 3157 strain includes a sequence of SEQ ID NO 24.

In a specific exemplary embodiment of the present disclosure, the recombinant expression construct includes a multiple cloning site (MCS) for inserting a transgene.

For example, BamHI and XbaI sites may be used when the transgene is human hepatocyte growth factor (HGF), and KpnI and ApaI sites may be used for SARS-COV-2 spike or RBD (receptor-binding domain), although not being limited thereto.

In the present specification, the term "transgene" refers to one or more polynucleotide or polynucleotide region encoded in a recombinant expression construct, an expression product of the polynucleotide or polynucleotide region, or a polynucleotide or a modulatory (or regulatory) nucleic acid encoding the polypeptide or polynucleotide region.

In a specific exemplary embodiment of the present disclosure, the transgene may be a polynucleotide encoding a therapeutic target peptide for sustained expression or a DNA or RNA vaccine for prevention or treatment of a disease.

In a specific exemplary embodiment of the present disclosure, the recombinant expression construct further includes a polyadenylation sequence (pA).

Specifically, the polyadenylation sequence includes an hGH (human growth hormone) pA sequence, a bGH (bovine growth hormone) pA sequence, an SV40 (simian vacuolating virus 40) early pA sequence, an SV40 late pA sequence, etc., although not being limited thereto.

In a specific exemplary embodiment of the present disclosure, the polyadenylation sequence includes a nucleotide sequence selected from a group consisting of SEQ ID NOS 29-32.

In a specific exemplary embodiment of the present disclosure, the recombinant expression construct further includes an antibiotic resistance gene.

In the present specification, the term "antibiotic resistance gene" refers to a gene inserted into a plasmid to confer drug resistance to ensure the survival of a microorganism even after exposure to an antibiotic. In most cases, it is used to screen individuals having a desired plasmid.

Specifically, the antibiotic resistance gene includes ampicillin, kanamycin, neomycin, chloramphenicol, gentamicin, streptomycin, tetracycline, erythromycin, vancomycin, penicillin, spectinomycin, chloramphenicol, sulfadiazine and trimethoprim resistance genes, although not being limited thereto.

In a specific exemplary embodiment of the present disclosure, the antibiotic resistance gene includes a gene sequence selected from a group consisting of neomycin resistance gene, kanamycin resistance gene (SEQ ID NO 28) and a combination thereof.

In a specific exemplary embodiment of the present disclosure, the recombinant expression construct has a cleavage map of FIG. 4.

In another aspect of the present disclosure, the present disclosure provides a recombinant expression construct for expressing a transgene, which includes the following constituents, wherein the transgene can be transcribed and translated in a host cell:
(a) a transgene; and
(b) a regulatory and transcribed region operationally linked (operably linked) to the transgene (regulatory and transcribed region), wherein the regulatory and transcribed region includes a sequence of SEQ ID NO 24.

The sequence of SEQ ID NO 24 is a sequence having homology to sequence derived from the full HCMV IE regulatory and transcribed region sequence of the HCMV 3157 strain.

In a specific exemplary embodiment of the present disclosure, the recombinant expression construct for expressing a transgene exhibits increased expression of a transgene as compared to when a regulatory and transcribed region selected from a group consisting of the full HCMV IE regulatory and transcribed region sequence of the HCMV Towne strain of SEQ ID NO 20, the full HCMV IE regulatory and transcribed region sequence of the HCMV AD169 strain of SEQ ID NO 22 and the full HCMV IE regulatory and transcribed region sequence of the HCMV CINCY and Towne strain (CINCY+Towne fusion) of SEQ ID NO 26 is inserted.

When a transgene is loaded, the recombinant expression construct of the present disclosure may increase the expression of the transgene by 10% or more, specifically 20% or more, more specifically 30% or more, most specifically 40% or more, as compared to when the full HCMV IE regulatory and transcribed region sequence of the HCMV Towne strain, the full HCMV IE regulatory and transcribed region sequence of the HCMV AD169 strain or the full HCMV IE regulatory and transcribed region sequence of the HCMV CINCY and Towne strain is loaded.

In a specific exemplary embodiment of the present disclosure, the recombinant expression construct of the present disclosure has homology to the full HCMV IE regulatory and transcribed region sequence of the HCMV 3157 strain of at least 80% or higher, at least 85% or higher or at least 90% or higher.

When present in the recombinant expression construct of the present disclosure, a sequence having homology to the full HCMV IE regulatory and transcribed region sequence of the HCMV 3157 strain maintains the expression level of the transgene at a comparable or similar level.

In the present disclosure, "maintains at a similar level" means that the expression level is decreased or increased by specifically 30% or less, more specifically 20% or less, most specifically 10% or less, with respect to the expression level of the transgene of a compared subject as 100%.

When a transgene is loaded, the recombinant expression construct of the present disclosure may greatly increase the expression efficiency of the transgene, and a sequence exhibiting expression efficiency comparable to that when the full HCMV IE regulatory and transcribed region sequence of the HCMV 3157 strain is inserted or expression efficiency of 90% or higher may be included in the sequence having homology.

In an exemplary embodiment of the present disclosure, the transgene may be a nucleotide sequence (e.g., HGF gene, variant gene thereof, etc.) encoding a peptide for treating a specific disease, which is for sustained expression in the body of a subject or a patient.

In an exemplary embodiment of the present disclosure, the transgene may be a DNA or RNA vaccine sequence (e.g., SARS-COV-2 spike gene, SARS-COV-2 spike RBD gene, etc.) for prevention of a specific disease (e.g., coronavirus), which is for sustained expression in the body of a subject or a patient.

In the present specification, the term "HGF variant" refers to an HGF polypeptide having an amino acid sequence that is at least 80% identical to an HGF amino acid sequence naturally occurring in animals, including all allelic variants. For example, the HGF variant includes normal or wild-type HGF, various variants of HGF (e.g., splicing variants and deleted variant) and heterotypes.

In the present specification, the "HGF variant" may be a hybrid HGF gene that can simultaneously express two heterotypes of HGF (HGF and dHGF) (see Korean Patent Registration No. 10-0562824). Specifically, the "hybrid HGF gene" may be a hybrid HGF gene with the intron 4 of the human HGF gene or a fragment sequence thereof inserted between exon 4 and exon 5 of HGF cDNA (e.g., SEQ ID NOS 16-18), which has high gene expression efficiency and can simultaneously express the two heterotypes of HGF and dHGF (deleted variant of HGF).

According to the gene therapy strategy of the present disclosure, it is preferred in terms of therapeutic effect to use one or more nucleotide sequence that encodes two or more heterotypes of HGF. The nucleotide sequence that encodes two or more heterotypes of HGF may be provided as a single polynucleotide.

Also, in the present specification, the "HGF variant gene" may be an HGF-X7 gene (SEQ ID NO 17) (see Korean Patent Registration No. 10-0562824).

Also, in the present specification, the "HGF variant gene" may be a deleted variant of HGF (dHGF) gene (SEQ ID NO 19) (see Korean Patent Registration No. 10-0562824). The term "dHGF" used in the present specification refers to a deleted variant of the HGF protein produced by alternative splicing of the HGF gene in an animal, specifically a mammal, more specifically human HGF consisting of 723 amino acids with deletion of five amino acids (F, L, P, S and S) in the first kringle domain of the alpha chain from the full HGF sequence (728 amino acids).

In the present specification, the "SARS-COV-2 spike gene" may be a gene sequence of SEQ ID NO 4.

In the present specification, the "SARS-COV-2 spike RBD gene" may be a gene sequence of SEQ ID NO 9.

In another aspect of the present disclosure, the present disclosure provides a host cell transduced, transfected or transformed with the recombinant expression construct or the recombinant expression construct for expressing a transgene.

In the present disclosure, the term "host cell" refers to a cell in an organism including a eukaryote and a prokaryote, to which a gene capable of replicating the expression construct (e.g., vector) or a gene encoded by the expression construct can be expressed can be introduced. In the present disclosure, the term "transduction" includes the meaning of transfection or transformation. The host cell may be transduced, transfected or transformed with the expression construct, and this means a process whereby an exogenous nucleic acid molecule is delivered or introduced into the host cell.

As the host cell of the present disclosure, a eukaryotic cell, specifically an insect cell or a mammalian cell may be used, although not being limited thereto. More specifically, the insect cell may be Sf9, and the mammal cell may be HEK293, HeLa, C2C12, ARPE-19, RPE-1, HepG2, Hep3B, Huh-7, C8D1a, Neuro2A, CHO, MES13, BHK-21, COS7, COP5, A549, MCF-7, HC70, HCC1428, BT-549, PC3, LNCaP, Capan-1, Panc-1, MIA PaCa-2, SW480, HCT166, LoVo, A172, MKN-45, MKN-74, Kato-III, NCI-N87, HT-144, SK-MEL-2, SH-SY5Y, C6, HT-22, PC-12, NIH3T3, etc.

Furthermore, the recombinant expression construct of the present disclosure for expressing a transgene may be used to directly deliver a gene for therapeutic or preventive purpose into a host cell of a mammal.

In another aspect of the present disclosure, the present disclosure provides a method for preparing the recombinant expression construct.

In another aspect of the present disclosure, the present disclosure provides a method for preparing the recombinant expression construct for expressing a transgene.

In an exemplary embodiment of the present disclosure, the method for preparing the recombinant expression construct of the present disclosure includes a step of inserting a sequence of SEQ ID NO 24 into a pVAX1 vector. For example, it may be prepared by inserting the full HCMV IE regulatory and transcribed region of the HCMV 3157 strain of SEQ ID NO 24 after removing a promoter from the pVAX1 vector.

In a specific exemplary embodiment of the present disclosure, the preparation method further includes a step of inserting a transgene into the recombinant expression construct.

In another aspect of the present disclosure, the present disclosure provides a therapeutic use of the recombinant expression construct for expressing a transgene.

In another aspect of the present disclosure, the present disclosure provides a method for expressing a transgene, which includes a step of administering a therapeutically effective amount of the recombinant expression construct for expressing a transgene to a subject in need thereof.

In a specific exemplary embodiment of the present disclosure, the expression may be expression in vivo.

In another aspect of the present disclosure, the present disclosure provides a pharmaceutical composition containing a pharmaceutically effective amount of the recombinant expression construct for expressing a transgene and a pharmaceutically acceptable carrier.

The pharmaceutically acceptable carrier used in the pharmaceutical composition of the present disclosure is one commonly used in formulation and may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto. The pharmaceutical composition of the present disclosure may further contain, in addition to the above-described ingredients, a lubricant, a wetting agent, a sweetener, a flavorant, an emulsifier, a suspending agent, a preservative, etc. Suitable pharmaceutically acceptable carriers and formulations are described in detail in Remington's Pharmaceutical Sciences (19th ed., 1995).

The pharmaceutical composition of the present disclosure may be administered orally or parenterally. Specifically, it may be administered parenterally, e.g., via intravenous injection, transdermal administration, subcutaneous injection, intramuscular injection, intravitreal injection, subretinal injection, suprachoroidal injection, eye drop administration, intracerebroventricular injection, intrathecal injection, intraamniotic injection, intraarterial injection, intraarticular injection, intracardiac injection, intracavernous injection, intracerebral injection, intracisternal injection, intracoronary injection, intracranial injection, intradural injection, epidural injection, intrahippocampal injection, intranasal injection, intraosseous injection, intraperitoneal injection, intrapleural injection, intraspinal injection, intrathoracic injection, intrathymic injection, intrauterine injection, intravaginal injection, intraventricular injection, intravesical injection, subconjunctival injection, intratumoral injection, topical injection, etc.

An adequate administration dosage of the pharmaceutical composition of the present disclosure varies depending on various factors such as formulation method, administration method, the age, body weight, sex, pathological condition and diet of a patient, administration time, administration route, excretion rate and response sensitivity. An ordinarily skilled physician can easily determine and prescribe an administration dosage effective for desired treatment or prevention. In a specific exemplary embodiment of the present disclosure, a daily administration dosage of the pharmaceutical composition of the present disclosure is 0.0001-100 mg/kg.

The pharmaceutical composition of the present disclosure may be prepared into a unit-dose form by formulating using a pharmaceutically acceptable carrier and/or excipient or may be introduced into a multi-dose container according to a method that can be easily executed by those having ordinary knowledge in the art to which the present disclosure belongs. The formulation may be in the form of a solution in an oil or an aqueous medium, a suspension, an emulsion, an extract, a powder, a granule, a tablet or a capsule, and may further contain a dispersant or a stabilizer.

In another aspect of the present disclosure, the present disclosure provides a method for treating a disease, which includes a step of administering an effective amount of the recombinant expression construct or the recombinant virus to a subject.

In the present specification, the term "subject" refers to refers to an individual in need of administration of the composition of the present disclosure or the recombinant expression construct, and includes a mammal, a bird, a reptile, an amphibian, a fish, etc., without limitation.

In a specific exemplary embodiment of the present disclosure, the present disclosure relates to a gene therapy agent capable of achieving sustained expression of a transgene, a method for treating a disease or a method for preventing a disease.

Specifically, the disease desired to be prevented, ameliorated or treated in the present disclosure includes any disease that requires reduced drug administration or delaying of the infection or progress of the disease, although not being limited thereto. Specifically, the disease that requires reduced drug administration includes ischemic disease, neurological disease, kidney disease or liver disease, although not being limited thereto.

Specifically, the disease that requires delaying of the infection or progress of the disease includes coronavirus disease, although not being limited thereto.

The features and advantages of the present disclosure are summarized as follows:

(i) The present disclosure provides a novel recombinant expression construct pHP3.

(ii) The pHP3 of the present disclosure can be usefully used for a gene therapy or a DNA vaccine because it increases the expression efficiency of various transgenes by about 50% or more when compared with recombinant expression constructs derived from various HCMV strains.

DETAILED DESCRIPTION

Hereinafter, the present disclosure will be described in more detail through examples. However, these examples are only for describing the present disclosure more specifically, and it will be obvious to those having ordinary knowledge in the art to which the present disclosure belongs that the scope of the present disclosure is not limited by the examples.

EXAMPLES

Materials and Methods

Genes
1. Human Hepatocyte Growth Factor (HGF)

A gene of human hepatocyte growth factor (HGF) represented by SEQ ID NO 1 (see NCBI base sequence NM_000601.6) was synthesized by Genscript (USA). The prepared gene was amplified by PCR using primers of SEQ ID NOS 2 and 3 of Table 1 and was inserted into a vector.

2. SARS-COV-2 (2019-nCOV) Spike

A SARS-COV-2 spike gene represented by SEQ ID NO 4 was synthesized using Spike ORF mammalian expression plasmid (Codon Optimized) sold by Sino Biological as a template. Primary PCR was conducted using primers of SEQ ID NOS 5 and 6 of Table 1, and secondary PCR was conducted using primers of SEQ ID NOS 7 and 8 of Table 1 for addition of a signal peptide sequence.

3. SARS-COV-2 (2019-nCOV) Spike Receptor-Binding Domain (RBD)

A gene represented by SEQ ID NO 9 was synthesized using Spike ORF mammalian expression plasmid (Codon Optimized) sold by Sino Biological as a template. Primary PCR was conducted using primers of SEQ ID NOS 10 and 11 of Table 1, and secondary PCR was conducted using primers of SEQ ID NOS 12 and 13 of Table 1 for addition of a signal peptide sequence.

Plasmids

Figure 1:
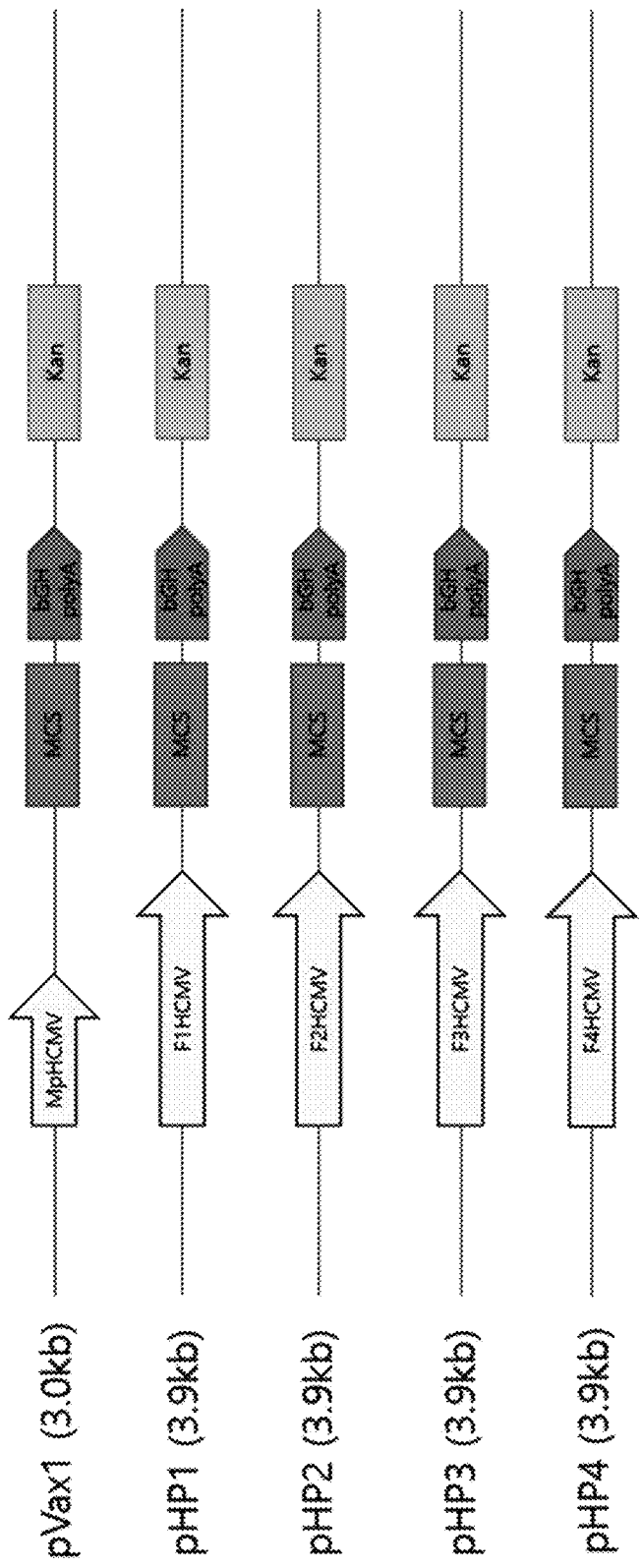
FIG. 1 schematically shows the structures of eukaryotic cell expression vectors having regulatory and transcribed regions of various HCMV strains.

The plasmids used in the present disclosure have the structures shown in FIG. 1. They were prepared as follows.

1. pVAX1 pVAX1-BMP2 (Plasmid #137909) was purchased from Addgene.

Figure 2:
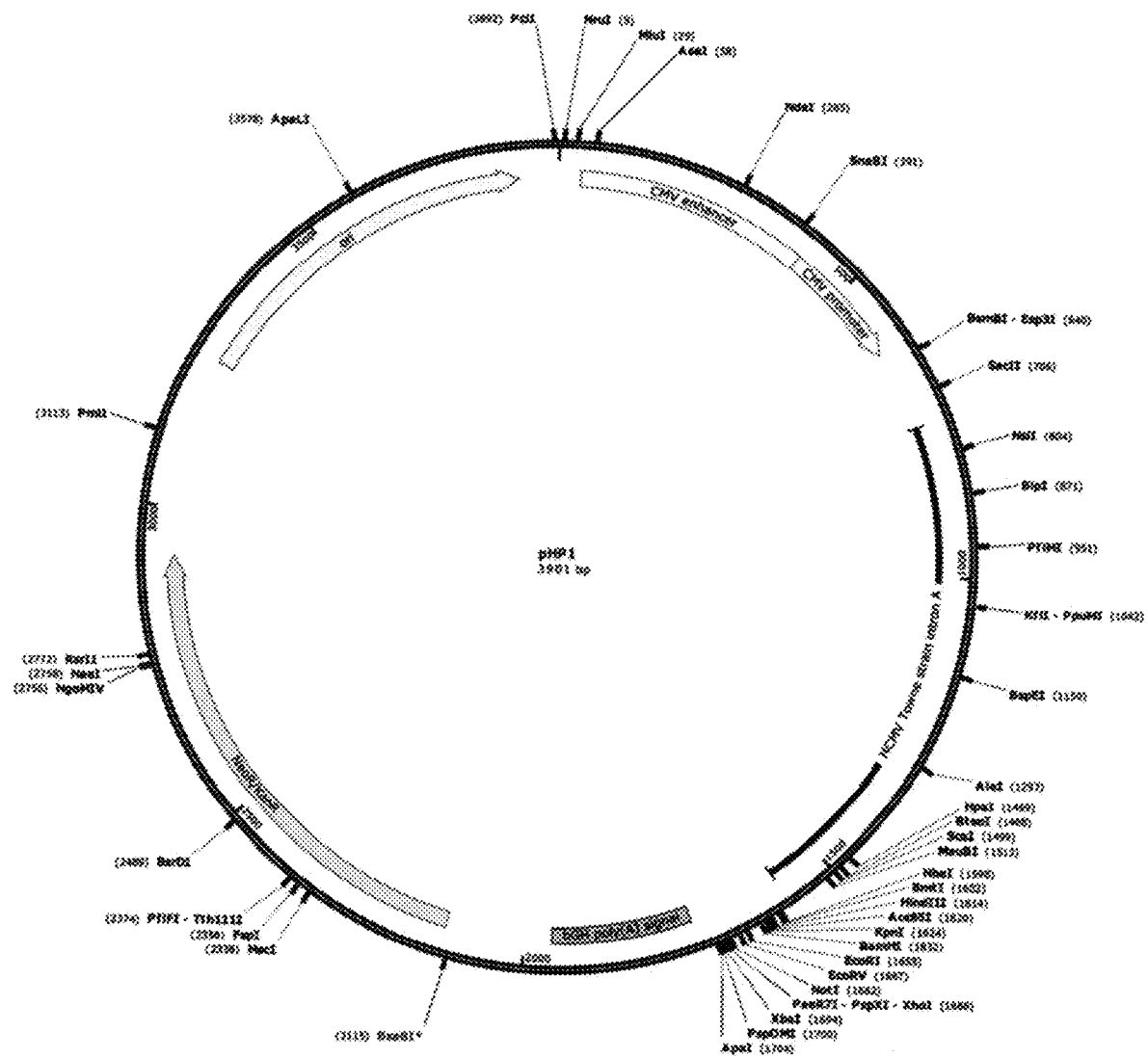
FIG. 2 shows the vector map of pHP1.

2. pHP1 pEQ276 (Plasmid #83945) purchased from Addgene was used as a template and the full HCMV promoter of the Towne strain was prepared by PCR using primers of SEQ ID NOS 14 and 15 of Table 1. pHP1 of SEQ ID NO 21 was prepared by cleaving the pVAX1 promoter with MluI and NheI and inserting the prepared promoter at the same restriction enzyme sites. The vector map of pHP1 is shown in FIG. 2.

3. pHP2

Figure 3:
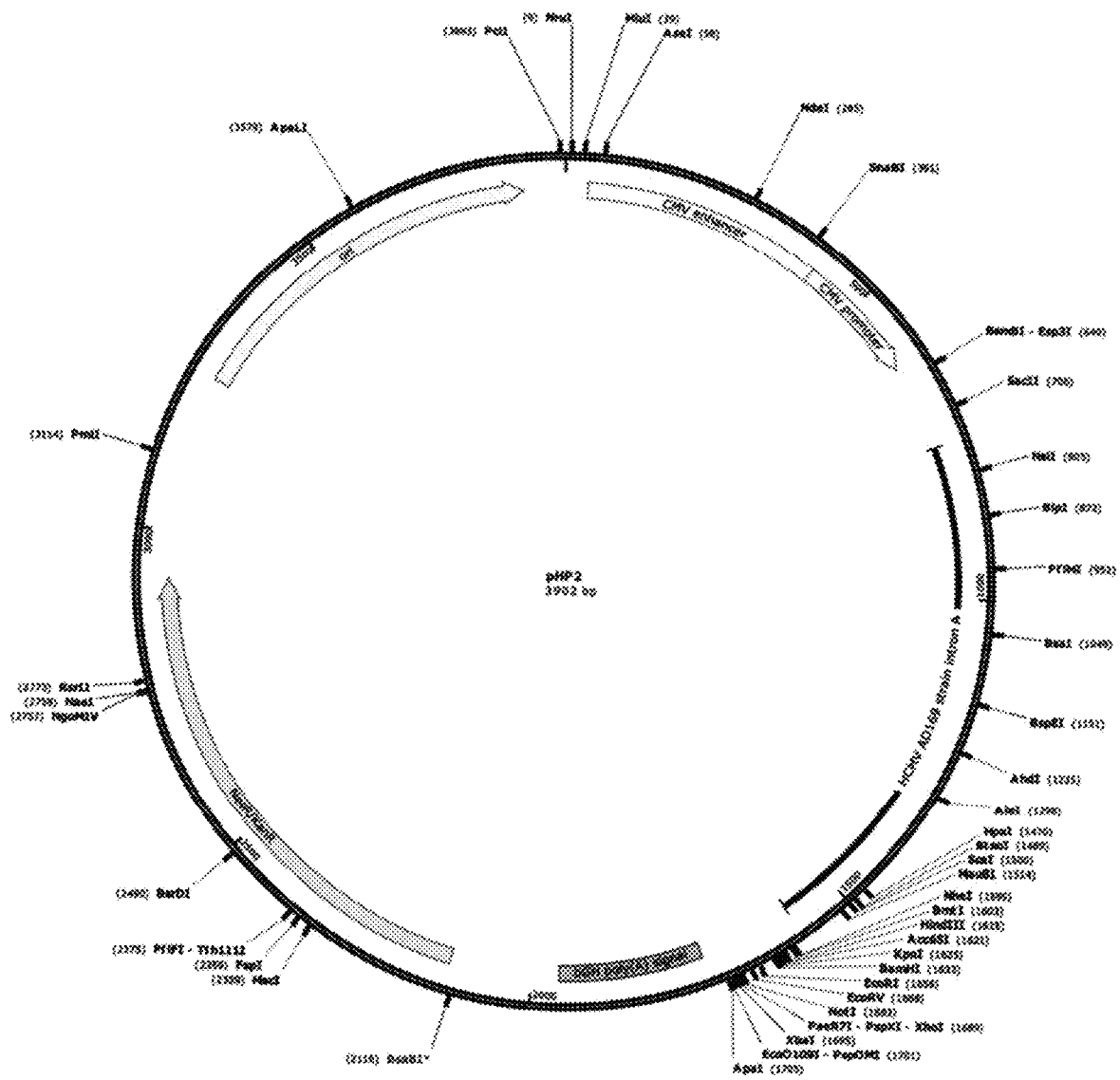
FIG. 3 shows the vector map of pHP2.

The full HCMV promoter of the AD169 strain was prepared by Bionics by referring to the NCBI base sequence X17403. pHP2 of SEQ ID NO 23 was prepared by cleaving the pVAX1 promoter with MluI and NheI and inserting the prepared promoter at the same restriction enzyme sites. The vector map of pHP2 is shown in FIG. 3.

4. pHP3

Figure 4:
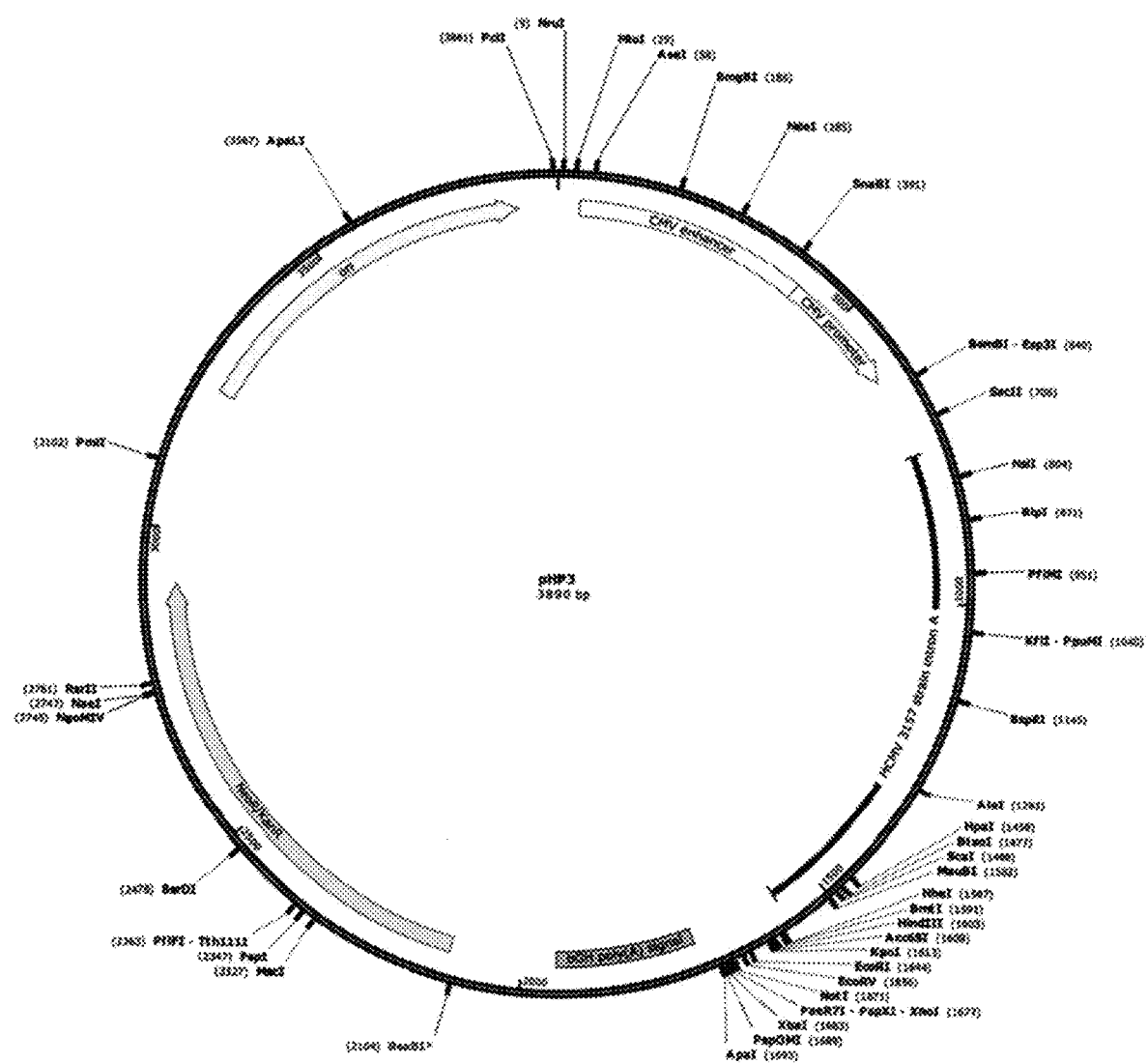
FIG. 4 shows the vector map of pHP3.

The full HCMV promoter of the 3157 strain was prepared by Bionics by referring to the NCBI base sequence GQ221974. PHP3 of SEQ ID NO 25 was prepared by cleaving the pVAX1 promoter with MluI and NheI and inserting the prepared promoter at the same restriction enzyme sites. The vector map of pHP3 is shown in FIG. 4.

5. pHP4

Figure 5:
FIG. 5 shows the vector map of pHP4.

The full HCMV promoter of the CINCY+Towne fusion strain was prepared by Bionics by referring to the NCBI base sequence GU980198.1. PHP4 of SEQ ID NO 27 was prepared by cleaving the pVAX1 promoter with MluI and NheI and inserting the prepared promoter at the same restriction enzyme sites. The vector map of pHP4 is shown in FIG. 5.

The prepared plasmid DNAs and genes are summarized in Table 2.

TABLE 1

| Primers | SEQ ID NO | Base sequence |
| --- | --- | --- |
| HGF (F) | 2 | GGATCCATGTGGGTGACCAAACTCCTGCCA |
| HGF (R) | 3 | GCGGCTCTAGACTATGACTGTGGTACCTTATATGT |
| Spike-1 (F) | 5 | CTGGTGGCCGCCGCCACACGGGTGCACAGCATGTTTGTGTTCCTGGTGCTGCTG |
| Spike-1 (R) | 6 | TCTAGATCAGGTGTAGTGCAGTTTCACTCCTTTC |
| Spike-2 (F) | 7 | CCGGGTACCATGGACTGGACCTGGATCCTGTTCCTGGTGGCCGCCGCCACA |
| Spike-2 (R) | 8 | CTAGTCTAGATCAGGTGTAGTGCAGTTTCACTCCTTTC |
| RBD-1 (F) | 10 | CTGGTGGCCGCCGCCACACGGGTGCACAGCCCAAACATCACCAACCTGTGTCCATTTGG |
| RBD-1 (R) | 11 | CTAGTCTAGATCACTCCAAGGTCTGTGGGTCCCTC |
| RBD-2 (F) | 12 | CCGGGTACCATGGACTGGACCTGGATCCTGTTCCTGGTGGCCGCCGCCACA |
| RBD-2 (R) | 13 | CTAGTCTAGATCACTCCAAGGTCTGTGGGTCCCTC |
| Towne (F) | 14 | ACGCGTTGACATTGATTATTGACTAGTTATTAATAG |
| Towne (R) | 15 | GCTAGCCGTGTCAAGGACGGTGACTGCAGAAAAGAC |

TABLE 2

| Gene or plasmid DNA | SEQ ID NO |
|---|---|
| Human hepatocyte growth factor (HGF) | 1 |
| HGF-X6 | 16 |
| HGF-X7 | 17 |
| HGF-X8 | 18 |
| dHGF (deleted variant of HGF) | 19 |
| SARS-COV-2 (2019-nCOV) spike | 4 |
| SARS-COV-2 (2019-nCOV) spike receptor binding domain (RBD) | 9 |
| Full HCMV IE sequence (1563 bp) of Towne strain (AY315197) | 20 |
| pHP1 | 21 |
| Full HCMV IE sequence (1564 bp) of AD169 strain (X17403) | 22 |
| pHP2 | 23 |
| Full HCMV IE sequence (1552 bp) of 3157 strain (GQ221974) | 24 |
| pHP3 | 25 |
| Full HCMV IE sequence (1563 bp) of CINCY + Towne fusion (GU980198.1) | 26 |
| PHP4 | 27 |
| Neomycin/kanamycin resistance gene | 28 |
| hGH pA | 29 |
| bGH pA | 30 |
| SV40 early pA | 31 |
| SV40 late pA | 32 |

Preparation of Plasmid DNAs Including Genes

Among the genes prepared above, each of a HGF gene and pHP plasmids was cleaved with BamHI and XbaI enzymes for 1 hour and fragments were separated by electrophoresis on agarose gel. The separated fragments were ligated for 30 minutes using T4 ligase and then transformed with *E. coli* and incubated overnight. The next day, DNA was isolated from the colony through mini-prep and identified with BamHI and XbaI.

Among the genes prepared above, each of SARS-COV-2 spike or spike RBD and pHP plasmids was cleaved with KpnI and ApaI enzymes for 1 hour and fragments were separated by electrophoresis on agarose gel. The separated fragments were ligated for 30 minutes using T4 ligase and then transformed with *E. coli* and incubated overnight. The next day, DNA was isolated from the colony through mini-prep and identified with KpnI and ApaI. After adding the *E. coli* supernatant containing the cloned DNA in two 200 mL flasks together with kanamycin and incubating overnight, plasmid DNAs were produced using a maxi prep. kit (Qiagen, USA).

EXPERIMENTAL RESULTS

Experimental Example 1: Comparison of HGF Protein Expression in Cells

In order to compare the expression level of the four pHP-HGF plasmid DNAs with the HGF gene inserted, HEK293 cells (Korean Cell Line Bank) cultured in DMEM (Dulbecco's modified Eagle's medium; Sigma-Aldrich, USA) containing 10% FBS (fetal bovine serum; Sigma-Aldrich, USA) were spread onto a 6-well plate (SPL, USA) with $1 \times 10^6$ cells per each well. The next day, when cell confluency was 60-80%, 3 μg of each plasmid DNA was mixed with 200 μL of a transfection reagent (jetPEI®, Polyplus transfection, USA). After incubation for 30 minutes at room temperature, the mixture was uniformly spread on each well. The next day, after replacing the medium with DMEM containing 10% FBS, the supernatant was collected 48 hours later and the expression of HGF protein was measured using an ELISA kit (R&D systems, USA).

Figure 6:
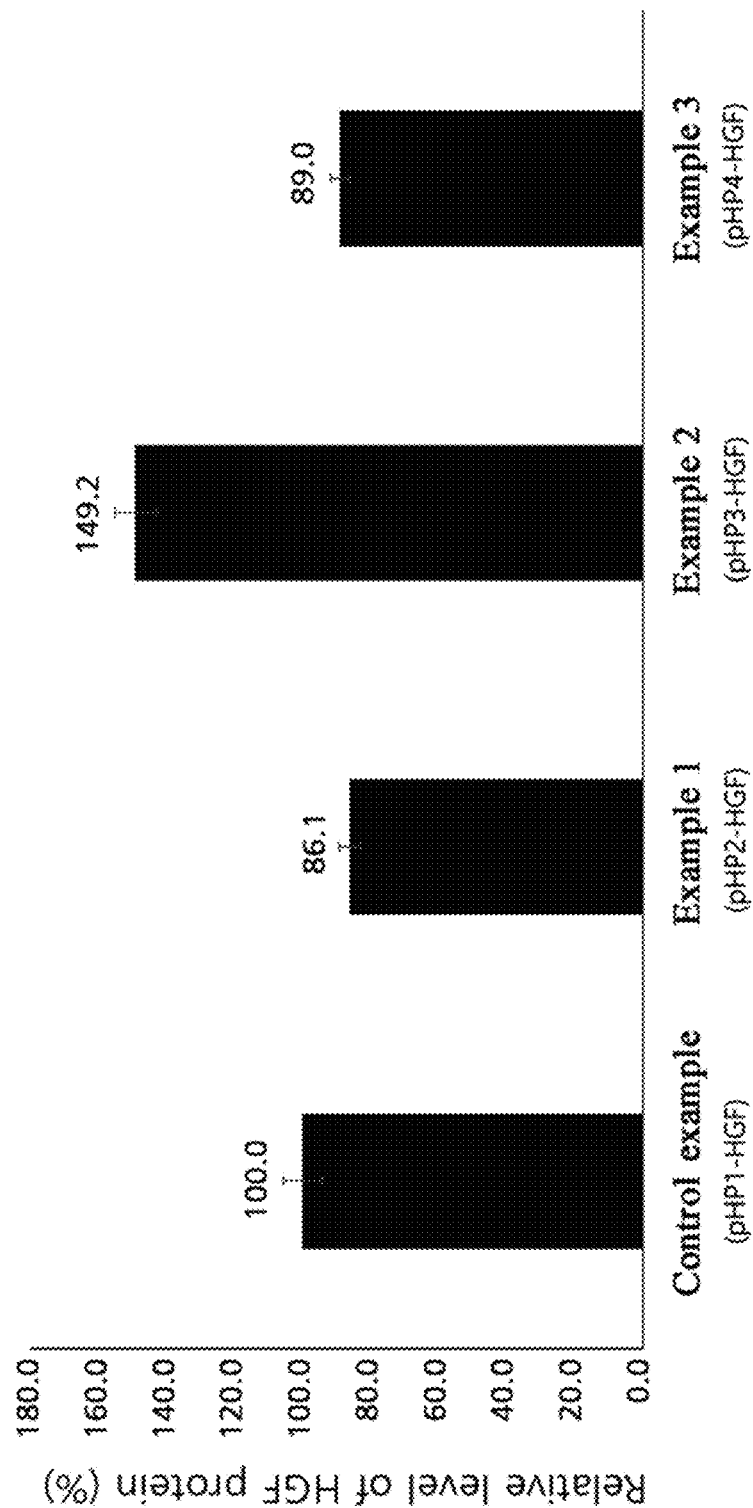
FIG. 6 shows a result of comparing the expression efficiency of pHP1, pHP2, pHP3 and pHP4 derived from various HCMV strains using a recombinant expression construct for expressing a transgene, which includes an HGF gene as a transgene.

As seen from FIG. 6, it was confirmed that the expression of the HGF protein was increased significantly by about 50% for the pHP3-HGF of Example 2 as compared to the pHP1-HGF of the control example. In contrast, Examples 1 and 3 showed decreased expression of the HGF protein as compared to the control example.

Experimental Example 2: Comparison of SARS-COV-2 Spike mRNA Expression in Cells In order to compare the expression level of the four pHP-spike plasmid DNAs with the SARS-COV-2 spike gene inserted, HEK293 cells (Korean Cell Line Bank) cultured in DMEM (Dulbecco's modified Eagle's medium; Sigma-Aldrich, USA) containing 10% FBS (fetal bovine serum; Sigma-Aldrich, USA) were spread onto a 6-well plate (SPL, USA) with $1 \times 10^6$ cells per each well. The next day, when cell confluency was 60-80%, 3 μg of each plasmid DNA was mixed with 200 μL of a transfection reagent (jetPEI®, Polyplus transfection, USA). After incubation for 30 minutes at room temperature, the mixture was uniformly spread on each well. The next day, after replacing the medium with DMEM containing 10% FBS, the cells were collected 48 hours later and the mRNA expression of the spike gene was measured by quantitative PCR. GAPDH was used as an internal control for normalization.

Figure 7:
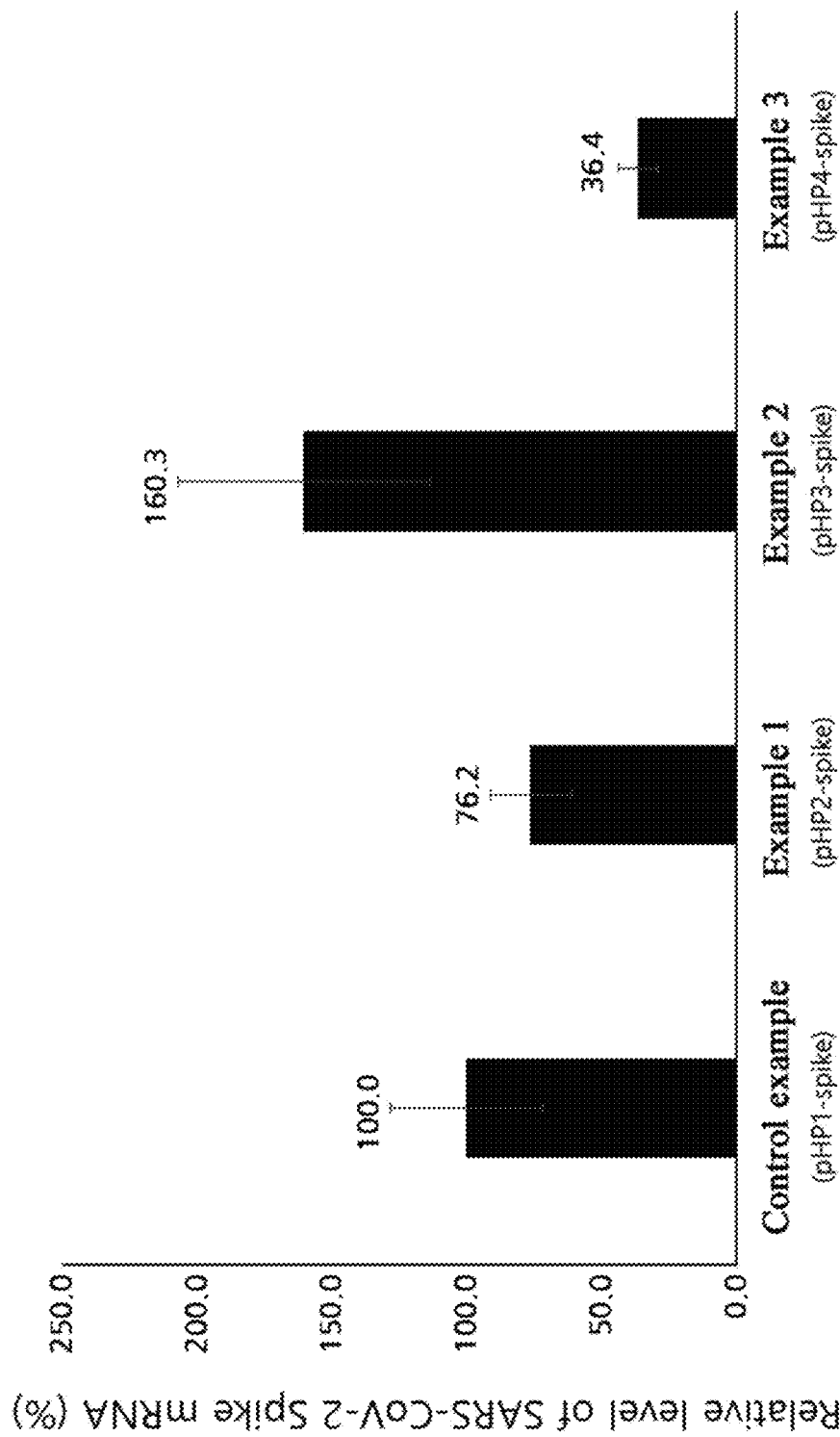
FIG. 7 shows a result of comparing the expression efficiency of pHP1, pHP2, pHP3 and pHP4 derived from various HCMV strains using a recombinant expression construct for expressing a transgene, which includes a SARS-COV-2 spike gene as a transgene.

As seen from FIG. 7, it was confirmed that mRNA expression was increased significantly by about 60% for the pHP3-spike of Example 2 as compared to the control example. In contrast, mRNA expression was decreased for Examples 1 and 3 as compared to the control example.

Experimental Example 3: Comparison of SARS-COV-2 RBD mRNA Expression in Cells In order to compare the expression level of the four pHP-RBD plasmid DNAs with the SARS-COV-2 spike RBD gene inserted, HEK293 cells (Korean Cell Line Bank) cultured in DMEM (Dulbecco's modified Eagle's medium; Sigma-Aldrich, USA) containing 10% FBS (fetal bovine serum; Sigma-Aldrich, USA) were spread onto a 6-well plate (SPL, USA) with $1 \times 10^6$ cells per each well. The next day, when cell confluency was 60-80%, 3 μg of each plasmid DNA was mixed with 200 μL of a transfection reagent (jetPEI®, Polyplus transfection, USA). After incubation for 30 minutes at room temperature, the mixture was uniformly spread on each well. The next day, after replacing the medium with DMEM containing 10% FBS, the cells were collected 48 hours later and the mRNA expression of the spike RBD gene was measured by quantitative PCR. GAPDH was used as an internal control for normalization.

Figure 8:
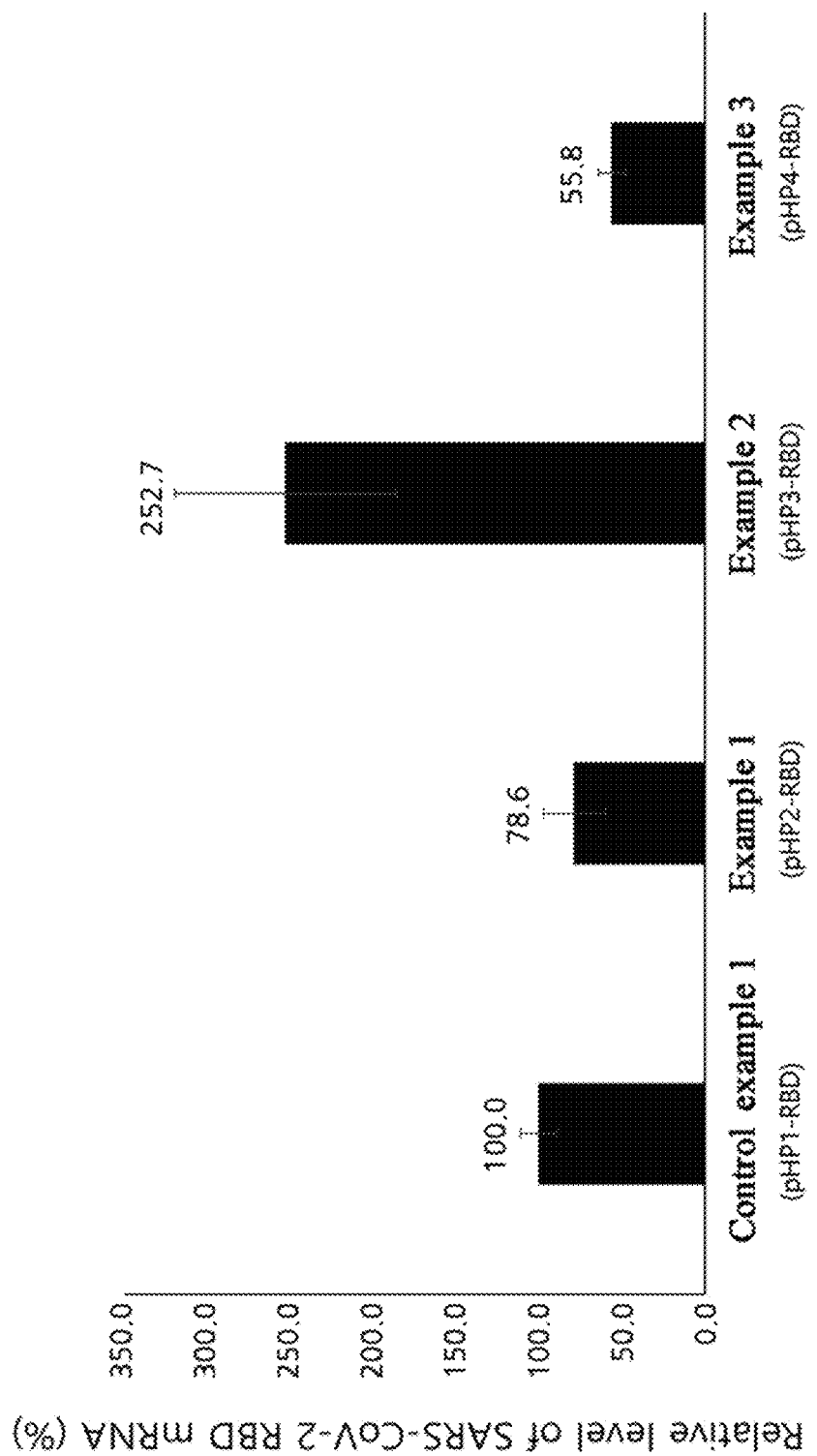
FIG. 8 shows a result of comparing the expression efficiency of pHP1, pHP2, pHP3 and pHP4 derived from various HCMV strains using a recombinant expression construct for expressing a transgene, which includes a SARS-COV-2 spike RBD (receptor-binding domain) gene as a transgene.

As seen from FIG. 8, it was confirmed that mRNA expression was increased significantly by about 150% for the pHP3-RBD of Example 2 as compared to the control example pHP1-RBD. In contrast, mRNA expression was decreased for Examples 1 and 3 as compared to the control example.

Through this, it was confirmed that there is difference in expression efficiency depending on the HCMV strains and the promoter of the HCMV 3157 strain, which is the basis of pHP3 exhibits the most superior expression efficiency.

Although the exemplary embodiments of the present disclosure have been described, those having ordinary knowledge in the art will be able to modify and change the present disclosure variously through supplementation, change, deletion, addition, etc. of constituent elements without departing from the technical idea of the present disclosure set forth in the claims, and such modifications and changes are included in the scope of the present disclosure.

What is claimed is:

1. A recombinant expression construct having the sequence of SEQ ID NO 25.

2. A recombinant expression construct for expressing a transgene, wherein the transgene can be transcribed and translated in a host cell, comprising:
 (a) a transgene; and
 (b) a regulatory and transcribed region operationally linked (operably linked) to the transgene, wherein the regulatory and transcribed region operationally linked (operably linked) to the transgene has the sequence of SEQ ID NO 25;
 wherein the transgene comprises hepatocyte growth factor (HGF) or a variant gene thereof, a SARS-COV-2 spike gene or a SARS-COV-2 spike RBD (receptor-binding domain) gene.

3. The recombinant expression construct for expressing a transgene according to claim 2, wherein the HGF or a variant gene thereof comprises a gene selected from a group consisting of SEQ ID NO 1 and SEQ ID NOS 16-19.

4. The recombinant expression construct for expressing a transgene according to claim 2, wherein the SARS-COV-2 spike gene comprises a gene of SEQ ID NO 4.

5. The recombinant expression construct for expressing a transgene according to claim 2, wherein the SARS-COV-2 spike RBD gene comprises a gene of SEQ ID NO 9.

6. An isolated host cell transduced with the recombinant expression construct according to claim 1.

7. An isolated host cell transduced with the recombinant expression construct according to claim 2.

* * * * *

SEQUENCE LISTING

<160> NUMBER OF SEQ ID NOS: 32

<210> SEQ ID NO 1
<211> LENGTH: 2187
<212> TYPE: DNA
<213> ORGANISM: Artificial Sequence
<220> FEATURE:
<223> OTHER INFORMATION: nucleotide sequence of HGF

<400> SEQUENCE: 1

| | | | | |
|---|---|---|---|---|
| atgtgggtga | ccaaactcct | gccagccctg | ctgctgcagc | atgtcctcct | gcatctcctc | 60 |
| ctgctcccca | tcgccatccc | ctatgcagag | ggacaaagga | aagaagaaa | tacaattcat | 120 |
| gaattcaaaa | aatcagcaaa | gactacccta | atcaaaatag | atccagcact | gaagataaaa | 180 |
| accaaaaaag | tgaatactgc | agaccaatgt | gctaatagat | gtactaggaa | taaaggactt | 240 |
| ccattcactt | gcaaggcttt | tgtttttgat | aaagcaagaa | aacaatgcct | ctggttcccc | 300 |
| ttcaatagca | tgtcaagtgg | agtgaaaaaa | gaatttggcc | atgaatttga | cctctatgaa | 360 |
| aacaaagact | acattagaaa | ctgcatcatt | ggtaaaggac | gcagctacaa | gggaacagta | 420 |
| tctatcacta | agagtggcat | caaatgtcag | ccctggagtt | ccatgatacc | acacgaacac | 480 |
| agcttttgc | cttcgagcta | tcggggtaaa | gacctacagg | aaaactactg | tcgaaatcct | 540 |
| cgaggggaag | aaggggggacc | ctggtgtttc | acaagcaatc | cagaggtacg | ctacgaagtc | 600 |
| tgtgacattc | ctcagtgttc | agaagttgaa | tgcatgacct | gcaatgggga | gagttatcga | 660 |
| ggtctcatgg | atcatacaga | atcaggcaag | atttgtcagc | gctgggatca | tcagacacca | 720 |
| caccggcaca | aattcttgcc | tgaaagatat | cccgacaagg | gctttgatga | taattattgc | 780 |
| cgcaatcccg | atggccagcc | gaggccatgg | tgctatactc | ttgaccctca | cacccgctgg | 840 |
| gagtactgtg | caattaaaac | atgcgctgac | aatactatga | atgacactga | tgttcctttg | 900 |
| gaaacaactg | aatgcatcca | aggtcaagga | gaaggctaca | gggcactgt | caataccatt | 960 |
| tggaatggaa | ttccatgtca | gcgttgggat | tctcagtatc | ctcacgagca | tgacatgact | 1020 |
| cctgaaaatt | tcaagtgcaa | ggacctacga | gaaaattact | gccgaaatcc | agatgggtct | 1080 |
| gaatcaccct | ggtgttttac | cactgatcca | aacatccgag | ttggctactg | ctcccaaatt | 1140 |
| ccaaactgtg | atatgtcaca | tggacaagat | tgttatcgtg | gaatggcaa | aaattatatg | 1200 |
| ggcaacttat | cccaaacaag | atctggacta | acatgttcaa | tgtgggacaa | gaacatggaa | 1260 |
| gacttacatc | gtcatatctt | ctgggaacca | gatgcaagta | agctgaatga | gaattactgc | 1320 |
| cgaaatccag | atgatgatgc | tcatggaccc | tggtgctaca | cgggaaatcc | actcattcct | 1380 |
| tgggattatt | gccctatttc | tcgttgtgaa | ggtgatacca | cacctacaat | agtcaattta | 1440 |
| gaccatcccg | taatatcttg | tgccaaaacg | aaacaattgc | gagttgtaaa | tgggattcca | 1500 |
| acacgaacaa | acataggatg | gatggttagt | ttgagataca | gaaataaaca | tatctgcgga | 1560 |
| ggatcattga | taaaggagag | ttgggttctt | actgcacgac | agtgtttccc | ttctcgagac | 1620 |
| ttgaaagatt | atgaagcttg | gcttggaatt | catgatgtcc | acggaagagg | agatgagaaa | 1680 |
| tgcaaacagg | ttctcaatgt | ttcccagctg | gtatatggcc | ctgaaggatc | agatctggtt | 1740 |
| ttaatgaagc | ttgccaggcc | tgctgtcctg | gatgattttg | ttagtacgat | tgatttacct | 1800 |
| aattatggat | gcacaattcc | tgaaaagacc | agttgcagtg | tttatggctg | gggctacact | 1860 |
| ggattgatca | actatgatgg | cctattacga | gtggcacatc | tctatataat | gggaaatgag | 1920 |
| aaatgcagcc | agcatcatcg | agggaaggtg | actctgaatg | agtctgaaat | atgtgctggg | 1980 |
| gctgaaaaga | ttggatcagg | accatgtgag | ggggattatg | gtggcccact | tgtttgtgag | 2040 |

-continued

```
caacataaaa tgagaatggt tcttggtgtc attgttcctg gtcgtggatg tgccattcca   2100
aatcgtcctg gtatttttgt ccgagtagca tattatgcaa aatggataca caaaattatt   2160
ttaacatata aggtaccaca gtcatag                                        2187
```

<210> SEQ ID NO 2
<211> LENGTH: 30
<212> TYPE: DNA
<213> ORGANISM: Artificial Sequence
<220> FEATURE:
<223> OTHER INFORMATION: Primer_HGF (F)

<400> SEQUENCE: 2

```
ggatccatgt gggtgaccaa actcctgcca                                       30
```

<210> SEQ ID NO 3
<211> LENGTH: 35
<212> TYPE: DNA
<213> ORGANISM: Artificial Sequence
<220> FEATURE:
<223> OTHER INFORMATION: Primer_HGF (R)

<400> SEQUENCE: 3

```
gcggctctag actatgactg tggtacctta tatgt                                 35
```

<210> SEQ ID NO 4
<211> LENGTH: 3876
<212> TYPE: DNA
<213> ORGANISM: Artificial Sequence
<220> FEATURE:
<223> OTHER INFORMATION: SARS-CoV-2(2019-nCoV) spike

<400> SEQUENCE: 4

```
atggactgga cctggatcct gttcctggtg gccgccgcca cacgggtgca cagcatgttt     60
gtgttcctgg tgctgctgcc actggtgtcc agccagtgtg tgaacctgac caccaggacc    120
caacttcctc ctgcctacac caactccttc accaggggag tctactaccc tgacaaggtg    180
ttcaggtcct ctgtgctgca cagcacccag gacctgttcc tgccattctt cagcaatgtg    240
acctggttcc atgccatcca tgtgtctggc accaatggca ccaagaggtt tgacaaccct    300
gtgctgccat tcaatgatgg agtctacttt gccagcacag agaagagcaa catcatcagg    360
ggctggattt ttggcaccac cctggacagc aagacccagt ccctgctgat tgtgaacaat    420
gccaccaatg tggtgattaa ggtgtgtgag ttccagttct gtaatgaccc attcctggga    480
gtctactacc acaagaacaa caagtcctgg atggagtctg agttcagggt ctactcctct    540
gccaacaact gtacctttga atatgtgagc caaccattcc tgatggactt ggagggcaag    600
cagggcaact tcaagaacct gagggagttt gtgttcaaga acattgatgg ctacttcaag    660
atttacagca aacacacacc aatcaacctg gtgagggacc tgccacaggg cttctctgcc    720
ttggaaccac tggtggacct gccaattggc atcaacatca ccaggttcca gaccctgctg    780
gctctgcaca ggtcctacct gacacctgga gactcctcct ctggctggac agcaggagca    840
gcagcctact atgtgggcta cctccaacca aggaccttcc tgctgaaata caatgagaat    900
ggcaccatca cagatgctgt ggactgtgcc ctggacccac tgtctgagac caagtgtacc    960
ctgaaatcct tcacagtgga gaagggcatc taccagacca gcaacttcag ggtccaacca   1020
acagagagca ttgtgaggtt tccaaacatc accaacctgt gtccatttgg agaggtgttc   1080
aatgccacca ggtttgcctc tgtctatgcc tggaacagga agaggattag caactgtgtg   1140
```

```
gctgactact ctgtgctcta caactctgcc tccttcagca ccttcaagtg ttatggagtg    1200
agcccaacca aactgaatga cctgtgtttc accaatgtct atgctgactc ctttgtgatt    1260
aggggagatg aggtgagaca gattgcccct ggacaaacag gcaagattgc tgactacaac    1320
tacaaactgc ctgatgactt cacaggctgt gtgattgcct ggaacagcaa caacctggac    1380
agcaaggtgg gaggcaacta caactacctc tacagactgt tcaggaagag caacctgaaa    1440
ccatttgaga gggacatcag cacagagatt taccaggctg gcagcacacc atgtaatgga    1500
gtggagggct tcaactgtta ctttccactc caatcctatg gcttccaacc aaccaatgga    1560
gtgggctacc aaccatacag ggtggtggtg ctgtcctttg aactgctcca tgcccctgcc    1620
acagtgtgtg gaccaaagaa gagcaccaac ctggtgaaga caagtgtgt gaacttcaac     1680 ttcaatggac tgacaggcac aggagtgctg acagagagca caagaagtt cctgccattc     1740 caacagtttg gcagggacat tgctgacacc acagatgctg tgagggaccc acagaccttg    1800
gagattctgg acatcacacc atgttccttt ggaggagtgt ctgtgattac acctggcacc    1860
aacaccagca accaggtggc tgtgctctac caggatgtga actgtactga ggtgcctgtg    1920
gctatccatg ctgaccaact tacaccaacc tggagggtct acagcacagg cagcaatgtg    1980
ttccagacca gggctggctg tctgattgga gcagagcatg tgaacaactc ctatgagtgt    2040
gacatcccaa ttggagcagg catctgtgcc tcctaccaga cccagaccaa cagcccaagg    2100
agggcaaggt ctgtgcaag ccagagcatc attgcctaca caatgagtct gggagcagag     2160
aactctgtgg cttacagcaa caacagcatt gccatcccaa ccaacttcac catctctgtg    2220
accacagaga ttctgcctgt gagtatgacc aagacctctg tggactgtac aatgtatatc    2280
tgtggagaca gcacagagtg tagcaacctg ctgctccaat atggctcctt ctgtacccaa    2340
cttaacaggg ctctgacagg cattgctgtg gaacaggaca gaacaccca ggaggtgttt     2400 gcccaggtga agcagattta caagacacct ccaatcaagg actttggagg cttcaacttc    2460
agccagattc tgcctgaccc aagcaagcca agcaagaggt ccttcattga ggacctgctg    2520
ttcaacaagg tgaccctggc tgatgctggc ttcatcaagc aatatggaga ctgtctggga    2580
gacattgctg ccaggaccct gatttgtgcc cagaagttca atggactgac agtgctgcct    2640
ccactgctga cagatgagat gattgcccaa tacacctctg ccctgctggc tggcaccatc    2700
acctctggct ggacctttgg agcaggagca gccctccaaa tcccatttgc tatgcagatg    2760
gcttacaggt tcaatggcat tggagtgacc cagaatgtgc tctatgagaa ccagaaactg    2820
attgccaacc agttcaactc tgccattggc aagattcagg actccctgtc cagcacagcc    2880
tctgccctgg gcaaactcca agatgtggtg aaccagaatg cccaggctct gaacaccctg    2940
gtgaagcaac tttccagcaa ctttggagcc atctcctctg tgctgaatga catcctgagc    3000
agactggaca aggtggaggc tgaggtccag attgacagac tgattacagg cagactccaa    3060
tccctccaaa cctatgtgac ccaacaactt atcagggctg ctgagattag gcatctgcc     3120 aacctggctc ccaccaagat gagtgagtgt gtgctgggac aaagcaagag ggtggacttc    3180
tgtggcaagg gctaccacct gatgagtttt ccacagtctg cccctcatgg agtggtgttc    3240
ctgcatgtga cctatgtgcc tgcccaggag aagaacttca ccacagcccc tgccatctgc    3300
catgatggca aggctcactt tccaagggag ggagtgtttg tgagcaatgg cacccactgg    3360
tttgtgaccc agaggaactt ctatgaacca cagattatca ccacagacaa cacctttgtg    3420
tctggcaact gtgatgtggt gattggcatt gtgaacaaca cagtctatga cccactccaa    3480
cctgaactgg actccttcaa ggaggaactg gacaaatact tcaagaacca caccagccct    3540
```
gatgtggacc tgggagacat ctctggcatc aatgcctctg tggtgaacat ccagaaggag 3600
attgacagac tgaatgaggt ggctaagaac ctgaatgagt ccctgattga cctccaagaa 3660
ctgggcaaat atgaacaata catcaagtgg ccatggtaca tctggctggg cttcattgct 3720
ggactgattg ccattgtgat ggtgaccata atgctgtgtt gtatgacctc ctgttgttcc 3780
tgtctgaaag gctgttgttc ctgtggctcc tgttgtaagt ttgatgagga tgactctgaa 3840
cctgtgctga aaggagtgaa actgcactac acctga 3876

<210> SEQ ID NO 5
<211> LENGTH: 54
<212> TYPE: DNA
<213> ORGANISM: Artificial Sequence
<220> FEATURE:
<223> OTHER INFORMATION: Primer_Spike-1 (F)

<400> SEQUENCE: 5
ctggtggccg ccgccacacg ggtgcacagc atgtttgtgt tcctggtgct gctg 54

<210> SEQ ID NO 6
<211> LENGTH: 34
<212> TYPE: DNA
<213> ORGANISM: Artificial Sequence
<220> FEATURE:
<223> OTHER INFORMATION: Primer_Spike-1 (R)

<400> SEQUENCE: 6
tctagatcag gtgtagtgca gtttcactcc tttc 34

<210> SEQ ID NO 7
<211> LENGTH: 51
<212> TYPE: DNA
<213> ORGANISM: Artificial Sequence
<220> FEATURE:
<223> OTHER INFORMATION: Primer_Spike-2 (F)

<400> SEQUENCE: 7
ccgggtacca tggactggac ctggatcctg ttcctggtgg ccgccgccac a 51

<210> SEQ ID NO 8
<211> LENGTH: 38
<212> TYPE: DNA
<213> ORGANISM: Artificial Sequence
<220> FEATURE:
<223> OTHER INFORMATION: Primer_Spike-2 (R)

<400> SEQUENCE: 8
ctagtctaga tcaggtgtag tgcagtttca ctcctttc 38

<210> SEQ ID NO 9
<211> LENGTH: 816
<212> TYPE: DNA
<213> ORGANISM: Artificial Sequence
<220> FEATURE:
<223> OTHER INFORMATION: SARS-CoV-2(2019-nCoV) spike receptor binding domain

<400> SEQUENCE: 9
atggactgga cctggatcct gttcctggtg gccgccgcca cacgggtgca cagcccaaac 60
atcaccaacc tgtgtccatt tggagaggtg ttcaatgcca ccaggtttgc ctctgtctat 120
gcctggaaca ggaagaggat tagcaactgt gtggctgact actctgtgct ctacaactct 180
gcctccttca gcaccttcaa gtgttatgga gtgagcccaa ccaaactgaa tgacctgtgt 240

```
ttcaccaatg tctatgctga ctcctttgtg attagggag atgaggtgag acagattgcc    300
cctggacaaa caggcaagat tgctgactac aactacaaac tgcctgatga cttcacaggc    360
tgtgtgattg cctggaacag caacaacctg acagcaagg tgggaggcaa ctacaactac    420
ctctacagac tgttcaggaa gagcaacctg aaaccatttg agaggacat cagcacagag    480 atttaccagg ctggcagcac accatgtaat ggagtggagg cttcaactg ttactttcca    540 ctccaatcct atggcttcca accaaccaat ggagtgggct accaaccata cagggtggtg    600
gtgctgtcct ttgaactgct ccatgcccct gccacagtgt gtggaccaaa gaagagcacc    660
aacctggtga gaacaagtg tgtgaacttc aacttcaatg gactgacagg cacaggagtg    720
ctgacagaga gcaacaagaa gttcctgcca ttccaacagt ttggcaggga cattgctgac    780
accacagatg ctgtgaggga cccacagacc ttggag                              816

<210> SEQ ID NO 10
<211> LENGTH: 59
<212> TYPE: DNA
<213> ORGANISM: Artificial Sequence
<220> FEATURE:
<223> OTHER INFORMATION: Primer_RBD-1 (F)

<400> SEQUENCE: 10
ctggtggccg ccgccacacg ggtgcacagc ccaaacatca ccaacctgtg tccatttgg    59

<210> SEQ ID NO 11
<211> LENGTH: 35
<212> TYPE: DNA
<213> ORGANISM: Artificial Sequence
<220> FEATURE:
<223> OTHER INFORMATION: Primer_RBD-1 (R)

<400> SEQUENCE: 11
ctagtctaga tcactccaag gtctgtgggt ccctc                              35

<210> SEQ ID NO 12
<211> LENGTH: 51
<212> TYPE: DNA
<213> ORGANISM: Artificial Sequence
<220> FEATURE:
<223> OTHER INFORMATION: Primer_RBD-2 (F)

<400> SEQUENCE: 12
ccgggtacca tggactggac ctggatcctg ttcctggtgg ccgccgccac a            51

<210> SEQ ID NO 13
<211> LENGTH: 35
<212> TYPE: DNA
<213> ORGANISM: Artificial Sequence
<220> FEATURE:
<223> OTHER INFORMATION: Primer_RBD-2 (R)

<400> SEQUENCE: 13
ctagtctaga tcactccaag gtctgtgggt ccctc                              35

<210> SEQ ID NO 14
<211> LENGTH: 36
<212> TYPE: DNA
<213> ORGANISM: Artificial Sequence
<220> FEATURE:
<223> OTHER INFORMATION: Primer_Towne (F)

<400> SEQUENCE: 14
```

```
acgcgttgac attgattatt gactagttat taatag                                36
```

<210> SEQ ID NO 15
<211> LENGTH: 36
<212> TYPE: DNA
<213> ORGANISM: Artificial Sequence
<220> FEATURE:
<223> OTHER INFORMATION: Primer_Towne (R)

<400> SEQUENCE: 15

```
gctagccgtg tcaaggacgg tgactgcaga aaagac                                36
```

<210> SEQ ID NO 16
<211> LENGTH: 4679
<212> TYPE: DNA
<213> ORGANISM: Artificial Sequence
<220> FEATURE:
<223> OTHER INFORMATION: nucleotide sequence of HGF-X6

<400> SEQUENCE: 16

```
atgtgggtga ccaaactcct gccagccctg ctgctgcagc atgtcctcct gcatctcctc      60
ctgctcccca tcgccatccc ctatgcagag ggacaaagga aagaagaaa tacaattcat      120
gaattcaaaa aatcagcaaa gactacccta atcaaaatag atccagcact gaagataaaa     180
accaaaaaag tgaatactgc agaccaatgt gctaatagat gtactaggaa taaggactt      240
ccattcactt gcaaggcttt tgttttgat aaagcaagaa acaatgcct ctggttcccc       300
ttcaatagca tgtcaagtgg agtgaaaaa gaatttggcc atgaatttga cctctatgaa      360
aacaaagact acattagaaa ctgcatcatc ggtaaaggac gcagctacaa gggaacagta     420
tctatcacta gagtggcat caaatgtcag ccctggagtt ccatgatacc acgaacac        480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa acaatatct taccttaatg cctcaatttg tagatctcgg     720
tatttgtgga tcccttcctt tctacctgta tttgtcctaa taaattgttg acttattaat    780
tcactacttc ctcacagctt tttttggct ttacaaatcc actggaaagg tatatgggtg     840
tatcactttg tgtatttcgg tgtgcatgtg tagaggggac aaaaatcctc tctcaaacta    900
taaatattga gtatttgtgt attgaacatt tgctataact actaggttc ttaaataatc     960
ttaatatata aaatgatata gaaaaaggga aattatagtt cgtattattc atctaagtga   1020
agagattaaa acccagggag taaataaatt gtctaaggac taaggttgta tactatttag   1080
gtgatagata tggggcaacc gtatgggttt atgattaac aaataaactt ctcaccactc    1140
taccatatca acttttccat aaaagagagc tatagtattc tttgcttaaa taaatttgat   1200
tagtgcatga cttcttgaaa acatataaag caaaagtcac atttgattct atcgaaaag    1260
tgagtaagcc atggcccaaa caaagatgc attaaaatat tctggaatga tggagctaaa   1320
agtaagaaaa atgactttt aaaaagttt actgttagga attgtgaaat tatgctgaat    1380
tttagttgca ttataatttt tgtcagtcat acggtctgac aacctgtctt atttctattt   1440
ccccatatga ggaatgctag ttaagtatgg atattaacta ttactactta gatgcattga   1500
agttgcataa tatggataat acttcactgg ttccctgaaa atgtttagtt agtaataagt   1560
ctcttacact atttgtttg tccaataatt tatattttct gaagacttaa ctctagaata   1620
cactcatgtc aaaatgaaag aatttcattg caaaatattg cttggtacat gacgcatacc   1680
```

```
tgtatttgtt ttgtgtcaca acatgaaaaa tgatggttta ttagaagttt cattgggtag    1740
gaaacacatt tgaatggtat ttactaagat actaaaatcc ttggacttca ctctaattt     1800
agtgccattt agaactcaag gtctcagtaa aagtagaaat aaagcctgtt aacaaaacac    1860
aagctgaata ttaaaaatgt aactggattt tcaaagaaat gtttactggt attacctgta    1920
gatgtatatt ctttattatg atcttttgtg taaagtctgg cagacaaatg caatatctaa    1980
ttgttgagtc caatatcaca agcagtacaa agtataaaa aagacttggc cttttctaat     2040
gtgttaaaat actttatgct ggtaataaca ctaagagtag ggcactagaa attttaagtg    2100
aagataatgt gttgcagtta ctgcactcaa tggcttacta ttataaacca aaactgggat    2160
cactaagctc cagtcagtca aaatgatcaa aattattgaa gagaataagc aattctgttc    2220
tttattagga cacagtagat acagactaca aagtggagtg tgcttaataa gaggtagcat    2280
ttgttaagtg tcaattactc tattatccct tggagcttct caaaataacc atataaggtg    2340
taagatgtta aaggttatgg ttacactcag tgcacaggta agctaatagg ctgagagaag    2400
ctaaattact tactggggtc tcacagtaag aaagtgagct gaagtttcag cccagattta    2460
actggattct gggctcttta ttcatgttac ttcatgaatc tgtttctcaa ttgtgcagaa    2520
aaaggggggc tatttataag aaaagcaata acaaacaag taatgatctc aaataagtaa     2580
tgcaagaaat agtgagattt caaaatcagt ggcagcgatt tctcagttct gtcctaagtg    2640
gccttgctca atcacctgct atcttttagt ggagctttga aattatgttt cagacaactt    2700
cgattcagtt ctagaatgtt tgactcagca aattcacagg ctcatctttc taacttgatg    2760
gtgaatatgg aaattcagct aaatggatgt taataaaatt caaacgtttt aaggacagat    2820
gaaaatgaca gaattttaag gtaaaatata tgaaggaata taagataaag gattttctta    2880
ccttcagcaa aaacataccc actaattagt aaaattaata ggcaaaaaaa agttgcatgc    2940
tcttatactg taatgattat cattttaaaa ctagcttttt gccttcgagc tatcggggta    3000
aagacctaca ggaaaactac tgtcgaaatc ctcgagggga agaaggggga ccctggtgtt    3060
tcacaagcaa tccagaggta cgctacgaag tctgtgacat tcctcagtgt tcagaagttg    3120
aatgcatgac ctgcaatggg gagagttatc gaggtctcat ggatcataca gaatcaggca    3180
agatttgtca gcgctgggat catcagacac cacaccggca caaattcttg cctgaaagat    3240
atcccgacaa gggctttgat gataattatt gccgcaatcc cgatggccag ccgaggccat    3300
ggtgctatac tcttgaccct cacacccgct gggagtactg tgcaattaaa acatgcgctg    3360
acaatactat gaatgacact gatgttcctt tggaaacaac tgaatgcatc caaggtcaag    3420
gagaaggcta caggggcact gtcaatacca tttggaatgg aattccatgt cagcgttggg    3480
attctcagta tcctcacgag catgacatga ctcctgaaaa tttcaagtgc aaggacctac    3540
gagaaaatta ctgccgaaat ccagatgggt ctgaatcacc ctggtgtttt accactgatc    3600
caaacatccg agttggctac tgctcccaaa ttccaaactg tgatatgtca catggacaag    3660
attgttatcg tgggaatggc aaaaattata tgggcaactt atcccaaaca agatctggac    3720
taacatgttc aatgtgggac aagaacatgg aagacttaca tcgtcatatc ttctgggaac    3780
cagatgcaag taagctgaat gagaaattact gccgaaatcc agatgatgat gctcatggac    3840
cctggtgcta cacgggaaat ccactcattc cttgggatta ttgccctatt tctcgttgtg    3900
aaggtgatac cacacctaca atagtcaatt tagaccatcc cgtaatatct tgtgccaaaa    3960
cgaaacaatt gcgagttgta aatgggattc caacacgaac aaacatagga tggatggtta    4020
```

| | |
|---|---|
| gtttgagata cagaaataaa catatctgcg gaggatcatt gataaaggag agttgggttc | 4080 |
| ttactgcacg acagtgtttc ccttctcgag acttgaaaga ttatgaagct tggcttggaa | 4140 |
| ttcatgatgt ccacggaaga ggagatgaga aatgcaaaca ggttctcaat gtttcccagc | 4200 |
| tggtatatgg ccctgaagga tcagatctgg ttttaatgaa gcttgccagg cctgctgtcc | 4260 |
| tggatgattt tgttagtacg attgatttac ctaattatgg atgcacaatt cctgaaaaga | 4320 |
| ccagttgcag tgtttatggc tggggctaca ctgattgat caactatgat ggcctattac | 4380 |
| gagtggcaca tctctatata tgggaaatg agaaatgcag ccagcatcat cgagggaagg | 4440 |
| tgactctgaa tgagtctgaa atatgtgctg gggctgaaaa gattggatca ggaccatgtg | 4500 |
| aggggattat tggtggccca cttgtttgtg agcaacataa aatgagaatg gttcttggtg | 4560 |
| tcattgttcc tggtcgtgga tgtgccattc caaatcgtcc tggtattttt gtccgagtag | 4620 |
| catattatgc aaaatggata cacaaaatta ttttaacata aaggtacca cagtcatag | 4679 |

<210> SEQ ID NO 17
<211> LENGTH: 3679
<212> TYPE: DNA
<213> ORGANISM: Artificial Sequence
<220> FEATURE:
<223> OTHER INFORMATION: nucleotide sequence of HGF-X7

<400> SEQUENCE: 17

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgtttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatc ggtaaaggac gcagctacaa gggaacagta | 420 |
| tctatcacta gagtggcat caaatgtcag ccctggagtt ccatgatacc acacgaacac | 480 |
| aggtaagaac agtatgaaga aaagagatga agcctctgtc ttttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa acaatatct taccttaatg cctcaatttg tagatctcgg | 720 |
| tatttgtgga tcctgggtag gaaacacatt tgaatggtat ttactaagat actaaaatcc | 780 |
| ttggacttca ctctaatttt agtgccattt agaactcaag gtctcagtaa aagtagaaat | 840 |
| aaagcctgtt aacaaaacac aagctgaata ttaaaaatgt aactggattt tcaaagaaat | 900 |
| gtttactggt attacctgta gatgtatatt cttttatg atcttttgtg taaagtctgg | 960 |
| cagacaaatg caatatctaa ttgttgagtc caatatcaca agcagtacaa agtataaaa | 1020 |
| aagacttggc cttttctaat gtgttaaaat actttatgct ggtaataaca ctaagagtag | 1080 |
| ggcactagaa attttaagtg aagataatgt gttgcagtta ctgcactcaa tggcttacta | 1140 |
| ttataaacca aaactgggat cactaagctc cagtcagtca aaatgatcaa aattattgaa | 1200 |
| gagaataagc aattctgttc tttattagga cacagtagat acagactaca agtggagtg | 1260 |
| tgcttaataa gaggtagcat ttgttaagtg tcaattactc tattatccct tggagcttct | 1320 |
| caaaataacc atataaggtg taagatgtta aggttatgg ttacactcag tgcacaggta | 1380 |
| agctaatagg ctgagagaag ctaaattact tactgggtc tcacagtaag aaagtgagct | 1440 |

```
gaagtttcag cccagattta actggattct gggctcttta ttcatgttac ttcatgaatc   1500
tgtttctcaa ttgtgcagaa aaaggggc  tatttataag aaaagcaata aacaaacaag    1560
taatgatctc aaataagtaa tgcaagaaat agtgagattt caaaatcagt ggcagcgatt   1620
tctcagttct gtcctaagtg gccttgctca atcacctgct atcttttagt ggagctttga   1680
aattatgttt cagacaactt cgattcagtt ctagaatgtt tgactcagca aattcacagg   1740
ctcatctttc taacttgatg gtgaatatgg aaattcagct aaatgatgt  taataaaatt    1800 caaacgtttt aaggacagat gaaaatgaca gaattttaag gtaaaatata tgaaggaata   1860
taagataaag gattttctca ccttcagcaa aaacataccc actaattagt aaaattaata   1920
ggcaaaaaaa agttgcatgc tcttatactg taatgattat cattttaaaa ctagcttttt   1980
gccttcgagc tatcggggta aagacctaca ggaaaactac tgtcgaaatc ctcgagggga   2040
agaaggggga ccctggtgtt tcacaagcaa tccagaggta cgctacgaag tctgtgacat   2100
tcctcagtgt tcagaagttg aatgcatgac ctgcaatggg gagagttatc gaggtctcat   2160
ggatcataca gaatcaggca agatttgtca gcgctgggat catcagacac cacaccggca   2220
caaattcttg cctgaaagat atcccgacaa gggctttgat gataattatt gccgcaatcc   2280
cgatggccag ccgaggccat ggtgctatac tcttgaccct cacacccgct gggagtactg   2340
tgcaattaaa acatgcgctg acaatactat gaatgacact gatgttcctt ggaaacaac    2400 tgaatgcatc caaggtcaag gagaaggcta caggggcact gtcaatacca tttggaatgg   2460
aattccatgt cagcgttggg attctcagta tcctcacgag catgacatga ctcctgaaaa   2520
tttcaagtgc aaggacctac gagaaaatta ctgccgaaat ccagatgggt ctgaatcacc   2580
ctggtgtttt accactgatc caaacatccg agttggctac tgctcccaaa ttccaaactg   2640
tgatatgtca catggacaag attgttatcg tgggaatggc aaaaattata tgggcaactt   2700
atcccaaaca agatctggac taacatgttc aatgtgggac aagaacatgg aagacttaca   2760
tcgtcatatc ttctgggaac cagatgcaag taagctgaat gagaattact gccgaaatcc   2820
agatgatgat gctcatggac cctggtgcta cacgggaaat ccactcattc cttgggatta   2880
ttgccctatt tctcgttgtg aaggtgatac cacacctaca atagtcaatt tagaccatcc   2940
cgtaatatct tgtgccaaaa cgaaacaatt gcgagttgta aatgggattc aacacgaac    3000 aaacatagga tggatggtta gtttgagata cagaaataaa catatctgcg gaggatcatt   3060
gataaaggag agttgggttc ttactgcacg acagtgtttc ccttctcgag acttgaaaga   3120
ttatgaagct tggcttggaa ttcatgatgt ccacggaaga ggagatgaga aatgcaaaca   3180
ggttctcaat gtttcccagc tggtatatgg ccctgaagga tcagatctgg ttttaatgaa   3240
gcttgccagg cctgctgtcc tggatgattt tgttagtacg attgatttac ctaattatgg   3300
atgcacaatt cctgaaaaga ccagttgcag tgtttatggc tggggctaca ctggattgat   3360
caactatgat ggcctattac gagtggcaca tctctatata atgggaaatg agaaatgcag   3420
ccagcatcat cgagggaagg tgactctgaa tgagtctgaa atatgtgctg ggctgaaaaa   3480
gattggatca ggaccatgtg agggggatta tggtggccca cttgtttgtg agcaacataa   3540
aatgagaatg gttcttggtg tcattgttcc tggtcgtgga tgtgccattc caaatcgtcc   3600
tggtattttt gtccgagtag catattatgc aaaatggata cacaaaatta ttttaacata   3660
taaggtacca cagtcatag                                                3679
```

<210> SEQ ID NO 18

<211> LENGTH: 2729
<212> TYPE: DNA
<213> ORGANISM: Artificial Sequence
<220> FEATURE:
<223> OTHER INFORMATION: nucleotide sequence of HGF-X8

<400> SEQUENCE: 18

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aaagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgttttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatc ggtaaaggac gcagctacaa gggaacagta | 420 |
| tctatcacta gagtggcat caaatgtcag ccctggagtt ccatgatacc acacgaacac | 480 |
| aggtaagaac agtatgaaga aaagagatga agcctctgtc tttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa aacaatatct taccttaatg cctcaatttg tagatctcgg | 720 |
| tatttgtgga tccttatgtt tcagacaact tcgattcagt tctagaatgt ttgactcagc | 780 |
| aaattcacag gctcatcttt ctaacttgat ggtgaatatg gaattcagc taaatggatg | 840 |
| ttaataaaat tcaaacgttt taaggacaga tgaaaatgac agaattttaa ggtaaaatat | 900 |
| atgaaggaat ataagataaa ggattttttct accttcagca aaaacatacc cactaattag | 960 |
| taaaattaat aggcaaaaaa aagttgcatg ctcttatact gtaatgatta tcattttaaa | 1020 |
| actagctttt tgccttcgag ctatcggggt aaagacctac aggaaaacta ctgtcgaaat | 1080 |
| cctcgagggg aagaaggggg accctggtgt tcacaagca atccagaggt acgctacgaa | 1140 |
| gtctgtgaca ttcctcagtg ttcagaagtt gaatgcatga cctgcaatgg ggagagttat | 1200 |
| cgaggtctca tggatcatac agaatcaggc aagatttgtc agcgctggga tcatcagaca | 1260 |
| ccacaccggc acaaattctt gcctgaaaga tatcccgaca agggctttga tgataattat | 1320 |
| tgccgcaatc ccgatggcca gccgaggcca tggtgctata ctcttgaccc tcacacccgc | 1380 |
| tgggagtact gtgcaattaa acatgcgct gacaatacta tgaatgacac tgatgttcct | 1440 |
| ttggaaacaa ctgaatgcat ccaaggtcaa ggagaaggct acaggggcac tgtcaatacc | 1500 |
| atttggaatg gaattccatg tcagcgttgg gattctcagt atcctcacga gcatgacatg | 1560 |
| actcctgaaa atttcaagtg caaggaccta cgagaaaatt actgccgaaa tccagatggt | 1620 |
| ctgaatcacc ctggtgtttt accactgatc caaacatccg agttggctac tgctcccaaa | 1680 |
| ttccaaactg tgatatgtca catggacaag attgttatcg tgggaatggc aaaaattata | 1740 |
| tgggcaactt atcccaaaca agatctggac taacatgttc aatgtgggac aagaacatgg | 1800 |
| aagacttaca tcgtcatatc ttctgggaac cagatgcaag taagctgaat gagaattact | 1860 |
| gccgaaatcc agatgatgat gctcatggac cctggtgcta cacgggaaat ccactcattc | 1920 |
| cttgggatta ttgccctatt tctcgttgtg aaggtgatac cacacctaca atagtcaatt | 1980 |
| tagaccatcc cgtaatatct tgtgccaaaa cgaaacaatt gcgagttgta atgggattc | 2040 |
| caacacgaac aaacatagga tggatggtta gtttgagata cagaaataaa catatctgcg | 2100 |
| gaggatcatt gataaaggag agttgggttc ttactgcacg acagtgtttc ccttctcgag | 2160 |

```
acttgaaaga ttatgaagct tggcttggaa ttcatgatgt ccacggaaga ggagatgaga    2220
aatgcaaaca ggttctcaat gtttcccagc tggtatatgg ccctgaagga tcagatctgg    2280
ttttaatgaa gcttgccagg cctgctgtcc tggatgattt tgttagtacg attgatttac    2340
ctaattatgg atgcacaatt cctgaaaaga ccagttgcag tgtttatggc tggggctaca    2400
ctggattgat caactatgat ggcctattac gagtggcaca tctctatata atgggaaatg    2460
agaaatgcag ccagcatcat cgagggaagg tgactctgaa tgagtctgaa atatgtgctg    2520
gggctgaaaa gattggatca ggaccatgtg aggggggatta tggtggccca cttgtttgtg    2580
agcaacataa aatgagaatg gttcttggtg tcattgttcc tggtcgtgga tgtgccattc    2640
caaatcgtcc tggtattttt gtccgagtag catattatgc aaaatggata cacaaaatta    2700
ttttaacata taaggtacca cagtcatag                                     2729
```

<210> SEQ ID NO 19
<211> LENGTH: 2172
<212> TYPE: DNA
<213> ORGANISM: Artificial Sequence
<220> FEATURE:
<223> OTHER INFORMATION: nucleotide sequence of dHGF (deleted varient of HGF)

<400> SEQUENCE: 19

```
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgttttttgat aaagcaagaa acaatgcct ctggttcccc     300 ttcaatagca tgtcaagtgg agtgaaaaaa gaatttggcc atgaatttga cctctatgaa     360
aacaaagact acattagaaa ctgcatcatc ggtaaaggac gcagctacaa gggaacagta     420
tctatcacta gagtggcat caaatgtcag ccctggagtt ccatgatacc acacgaacac     480
agctatcggg gtaaagacct acaggaaaac tactgtcgaa atcctcgagg ggaagaaggg     540
ggaccctggt gtttcacaag caatccagag gtacgctacg aagtctgtga cattcctcag     600
tgttcagaag ttgaatgcat gacctgcaat ggggagagtt atcgaggtct catggatcat     660
acagaatcag gcaagatttg tcagcgctgg gatcatcaga caccacaccg gcacaaattc     720
ttgcctgaaa gatatcccga caagggcttt gatgataatt attgccgcaa tcccgatggc     780
cagccgaggc catggtgcta tactcttgac cctcacaccc gctgggagta ctgtgcaatt     840
aaaacatgcg ctgacaatac tatgaatgac actgatgttc ctttggaaac aactgaatgc     900
atccaaggtc aaggagaagg ctacaggggc actgtcaata ccatttggaa tggaattcca     960
tgtcagcgtt gggattctca gtatcctcac gagcatgaca tgactcctga aaatttcaag    1020
tgcaaggacc tacgagaaaa ttactgccga aatccagatg gtctgaatc accctggtgt    1080 tttaccactg atccaaacat ccgagttggc tactgctccc aaattccaaa ctgtgatatg    1140
tcacatggac aagattgtta tcgtgggaat ggcaaaaatt atatgggcaa cttatcccaa    1200
acaagatctg gactaacatg ttcaatgtgg gacaagaaca tggaagactt acatcgtcat    1260
atcttctggg aaccagatgc aagtaagctg aatgagaatt actgccgaaa tccagatgat    1320
gatgctcatg gaccctggtg ctacacggga aatccactca ttccttggga ttattgccct    1380
atttctcgtt gtgaaggtga taccacacct acaatagtca atttagacca tcccgtaata    1440
```

```
tcttgtgcca aaacgaaaca attgcgagtt gtaaatggga ttccaacacg aacaaacata   1500
ggatggatgg ttagtttgag atacagaaat aaacatatct gcggaggatc attgataaag   1560
gagagttggg ttcttactgc acgacagtgt ttcccttctc gagacttgaa agattatgaa   1620
gcttggcttg gaattcatga tgtccacgga agaggagatg agaaatgcaa acaggttctc   1680
aatgtttccc agctggtata tggccctgaa ggatcagatc tggtttttaat gaagcttgcc   1740 aggcctgctg tcctggatga ttttgttagt acgattgatt tacctaatta tggatgcaca   1800
attcctgaaa agaccagttg cagtgtttat ggctggggct acactggatt gatcaactat   1860
gatggcctat tacgagtggc acatctctat ataatgggaa atgagaaatg cagccagcat   1920
catcgaggga aggtgactct gaatgagtct gaaatatgtg ctggggctga aaagattgga   1980
tcaggaccat gtgagggga ttatggtggc ccacttgttt gtgagcaaca taaaatgaga   2040
atggttcttg gtgtcattgt tcctggtcgt ggatgtgcca ttccaaatcg tcctggtatt   2100
tttgtccgag tagcatatta tgcaaaatgg atacacaaaa ttattttaac atataaggta   2160
ccacagtcat ag                                                       2172

<210> SEQ ID NO 20
<211> LENGTH: 1563
<212> TYPE: DNA
<213> ORGANISM: Artificial Sequence
<220> FEATURE:
<223> OTHER INFORMATION: Towne strain (AY315197) full HCMV IE

<400> SEQUENCE: 20
tgacattgat tattgactag ttattaatag taatcaatta cggggtcatt agttcatagc     60
ccatatatgg agttccgcgt tacataactt acggtaaatg gcccgcctgg ctgaccgccc    120 aacgacccc gcccattgac gtcaataatg acgtatgttc ccatagtaac gccaataggg    180
actttccatt gacgtcaatg ggtggagtat ttacggtaaa ctgcccactt ggcagtacat    240
caagtgtatc atatgccaag tccgcccct attgacgtca atgacggtaa atggcccgcc    300
tggcattatg cccagtacat gaccttacgg gactttccta cttggcagta catctacgta    360
ttagtcatcg ctattaccat ggtgatgcgg ttttggcagt acaccaatgg gcgtggatag    420
cggtttgact cacggggatt tccaagtctc caccccattg acgtcaatgg gagtttgttt    480
tggcaccaaa atcaacggga ctttccaaaa tgtcgtaata accccgcccc gttgacgcaa    540
atgggcggta ggcgtgtacg gtgggaggtc tatataagca gagctcgttt agtgaaccgt    600
cagatcgcct ggagacgcca tccacgctgt tttgacctcc atagaagaca ccgggaccga    660
tccagcctcc gcggccggga acggtgcatt ggaacgcgga ttccccgtgc caagagtgac    720
gtaagtaccg cctatagact ctataggcac ccccttttgg ctcttatgca tgctatactg    780
tttttggctt ggggcctata cccccgct tccttatgct ataggtgatg gtatagctta    840
gcctataggt gtgggttatt gaccattatt gaccactccc ctattggtga cgatactttc    900
cattactaat ccataacatg gctctttgcc acaactatct ctattggcta tatgccaata    960
ctctgtcctt cagagactga cacggactct gtattttac aggatggggt cccattiatt   1020 atttacaaat tcacatatac aacaacgccg tcccccgtgc ccgcagtttt tattaaacat   1080
agcgtgggat ctccacgcga atctcgggta cgtgttccgg acatgggctc ttctccggta   1140
gcggcggagc ttcacatcc gagccctggt cccatgcctc cagcggctca tggtcgctcg   1200
gcagctcctt gctcctaaca gtggaggcca gacttaggca cagcacaatg cccaccacca   1260
```

| | |
|---|---:|
| ccagtgtgcc gcacaaggcc gtggcggtag ggtatgtgtc tgaaaatgag ctcggagatt | 1320 |
| gggctcgcac cgctgacgca gatggaagac ttaaggcagc ggcagaagaa gatgcaggca | 1380 |
| gctgagttgt tgtattctga taagagtcag aggtaactcc cgttgcggtg ctgttaacgg | 1440 |
| tggagggcag tgtagtctga gcagtactcg ttgctgccgc gcgcgccacc agacataata | 1500 |
| gctgacagac taacagactg ttcctttcca tgggtctttt ctgcagtcac cgtccttgac | 1560 |
| acg | 1563 |

<210> SEQ ID NO 21
<211> LENGTH: 3901
<212> TYPE: DNA
<213> ORGANISM: Artificial Sequence
<220> FEATURE:
<223> OTHER INFORMATION: pHP1

<400> SEQUENCE: 21

| | |
|---|---:|
| gactcttcgc gatgtacggg ccagatatac gcgttgacat tgattattga ctagttatta | 60 |
| atagtaatca attacggggt cattagttca tagcccatat atggagttcc gcgttacata | 120 |
| acttacggta aatggcccgc ctggctgacc gcccaacgac ccccgcccat tgacgtcaat | 180 |
| aatgacgtat gttcccatag taacgccaat agggactttc cattgacgtc aatgggtgga | 240 |
| gtatttacgg taaactgccc acttggcagt acatcaagtg tatcatatgc caagtccgcc | 300 |
| ccctattgac gtcaatgacg gtaaatggcc cgcctggcat tatgcccagt acatgacctt | 360 |
| acgggacttt cctacttggc agtacatcta cgtattagtc atcgctatta ccatggtgat | 420 |
| gcggttttgg cagtacacca atgggcgtgg atagcggttt gactcacggg gatttccaag | 480 |
| tctccacccc attgacgtca atgggagttt gttttggcac caaaatcaac gggactttcc | 540 |
| aaaatgtcgt aataaccccg ccccgttgac gcaaatgggc ggtaggcgtg tacggtggga | 600 |
| ggtctatata agcagagctc gtttagtgaa ccgtcagatc gcctggagac gccatccacg | 660 |
| ctgttttgac ctccatagaa gacaccggga ccgatccagc ctccgcggcc gggaacggtg | 720 |
| cattggaacg cggattcccc gtgccaagag tgacgtaagt accgcctata gactctatag | 780 |
| gcacacccct ttggctctta tgcatgctat actgttttg gctgggggcc tatacacccc | 840 |
| cgcttcctta tgctataggt gatggtatag cttagcctat aggtgtgggt tattgaccat | 900 |
| tattgaccac tcccctattg gtgacgatac tttccattac taatccataa catggctctt | 960 |
| tgccacaact atctctattg gctatatgcc aatactctgt ccttcagaga ctgacacgga | 1020 |
| ctctgtattt ttacaggatg ggtcccatt tattatttac aaattcacat atacaacaac | 1080 |
| gccgtccccc gtgcccgcag ttttattaa acatagcgtg gatctccac gcgaatctcg | 1140 |
| ggtacgtgtt ccggacatgg gctcttctcc ggtagcggcg gagcttccac atccgagccc | 1200 |
| tggtcccatg cctccagcgg ctcatggtcg ctcggcagct ccttgctcct aacagtggag | 1260 |
| gccagactta ggcacagcac aatgcccacc accaccagtg tgccgcacaa ggccgtggcg | 1320 |
| gtagggtatg tgtctgaaaa tgagctcgga gattgggctc gcaccgctga cgcagatgga | 1380 |
| agacttaagg cagcggcaga agaagatgca ggcagctgag ttgttgtatt ctgataagag | 1440 |
| tcagaggtaa ctcccgttgc ggtgctgtta acggtggagg gcagtgtagt ctgagcagta | 1500 |
| ctcgttgctg ccgcgcgcgc caccagacat aatagctgac agactaacag actgttcctt | 1560 |
| tccatgggtc ttttctgcag tcaccgtcct tgacacggct agcgtttaaa cttaagcttg | 1620 |
| gtaccgagct cggatccact agtccagtgt ggtggaattc tgcagatatc cagcacagtg | 1680 |
| gcggccgctc gagtctagag ggcccgttta aacccgctga tcagcctcga ctgtgccttc | 1740 |

```
tagttgccag ccatctgttg tttgcccctc cccgtgcct tccttgaccc tggaaggtgc    1800
cactcccact gtcctttcct aataaaatga ggaaattgca tcgcattgtc tgagtaggtg    1860
tcattctatt ctgggggtg gggtggggca ggacagcaag ggggaggatt gggaagacaa    1920
tagcaggcat gctggggatg cggtgggctc tatggcttct actgggcggt tttatggaca    1980
gcaagcgaac cggaattgcc agctggggcg ccctctggta aggttgggaa gccctgcaaa    2040
gtaaactgga tggctttctc gccgccaagg atctgatggc gcaggggatc aagctctgat    2100
caagagacag gatgaggatc gtttcgcatg attgaacaag atggattgca cgcaggttct    2160
ccggccgctt gggtggagag gctattcggc tatgactggg cacaacagac aatcggctgc    2220
tctgatgccg ccgtgttccg gctgtcagcg caggggcgcc cggttctttt tgtcaagacc    2280
gacctgtccg gtgccctgaa tgaactgcaa gacgaggcag cgcggctatc gtggctggcc    2340
acgacgggcg ttccttgcgc agctgtgctc gacgttgtca ctgaagcggg aagggactgg    2400
ctgctattgg gcgaagtgcc ggggcaggat ctcctgtcat ctcaccttgc tcctgccgag    2460
aaagtatcca tcatggctga tgcaatgcgg cggctgcata cgcttgatcc ggctacctgc    2520
ccattcgacc accaagcgaa acatcgcatc gagcgagcac gtactcggat ggaagccggt    2580
cttgtcgatc aggatgatct ggacgaagag catcaggggc tcgcgccagc cgaactgttc    2640
gccaggctca aggcgagcat gcccgacggc gaggatctcg tcgtgaccca tggcgatgcc    2700
tgcttgccga atatcatggt ggaaaatggc cgcttttctg gattcatcga ctgtggccgg    2760
ctgggtgtgg cggaccgcta tcaggacata gcgttggcta cccgtgatat tgctgaagag    2820
cttggcggcg aatgggctga ccgcttcctc gtgctttacg gtatcgccgc tcccgattcg    2880
cagcgcatcg ccttctatcg ccttcttgac gagttcttct gaattattaa cgcttacaat    2940
ttcctgatgc ggtattttct ccttacgcat ctgtgcggta tttcacaccg catacaggtg    3000
gcacttttcg gggaaatgtg cgcggaaccc ctatttgttt attttctaa atacattcaa    3060
atatgtatcc gctcatgaga caataaccct gataaatgct tcaataatag cacgtgctaa    3120
aacttcattt ttaatttaaa aggatctagg tgaagatcct ttttgataat ctcatgacca    3180
aaatccctta acgtgagttt tcgttccact gagcgtcaga ccccgtagaa aagatcaaag    3240
gatcttcttg agatcctttt tttctgcgcg taatctgctg cttgcaaaca aaaaaaccac    3300
cgctaccagc ggtggtttgt ttgccggatc aagagctacc aactcttttt ccgaaggtaa    3360
ctggcttcag cagagcgcag ataccaaata ctgtccttct agtgtagccg tagttaggcc    3420
accacttcaa gaactctgta gcaccgccta catacctcgc tctgctaatc ctgttaccag    3480
tggctgctgc cagtggcgat aagtcgtgtc ttaccgggtt ggactcaaga cgatagttac    3540
cggataaggc gcagcggtcg ggctgaacgg ggggttcgtg cacacagccc agcttggagc    3600
gaacgaccta caccgaactg agatacctac agcgtgagct atgagaaagc gccacgcttc    3660
ccgaagggag aaaggcggac aggtatccgg taagcggcag ggtcggaaca ggagagcgca    3720
cgagggagct tccaggggga aacgcctggt atctttatag tcctgtcggg tttcgccacc    3780
tctgacttga gcgtcgattt ttgtgatgct cgtcaggggg gcggagccta tggaaaaacg    3840
ccagcaacgc ggccttttta cggttcctgg cttttgctg ccttttgct cacatgttct    3900
t                                                                    3901

<210> SEQ ID NO 22
<211> LENGTH: 1564
<212> TYPE: DNA
```

<213> ORGANISM: Artificial Sequence
<220> FEATURE:
<223> OTHER INFORMATION: AD169 strain (X17403) full HCMV IE

<400> SEQUENCE: 22

```
tgacattgat tattgactag ttattaatag taatcaatta cggggtcatt agttcatagc      60
ccatatatgg agttccgcgt tacataactt acggtaaatg gcccgcctgg ctgaccgccc     120
aacgaccccc gcccattgac gtcaataatg acgtatgttc ccatagtaac gccaataggg     180
actttccatt gacgtcaatg ggtggagtat ttacggtaaa ctgcccactt ggcagtacat     240
caagtgtatc atatgccaag tacgcccccct attgacgtca atgacggtaa atggcccgcc    300
tggcattatg cccagtacat gaccttatgg gactttccta cttggcagta catctacgta     360
ttagtcatcg ctattaccat ggtgatgcgg ttttggcagt acatcaatgg gcgtggatag     420
cggtttgact cacggggatt tccaagtctc cacccccattg acgtcaatgg gagtttgttt    480
tggcaccaaa atcaacggga ctttccaaaa tgtcgtaaca actccgcccc attgacgcaa     540
atgggcggta ggcgtgtacg gtgggaggtc tatataagca gagctcgttt agtgaaccgt     600
cagatcgcct ggagacgcca tccacgctgt tttgacctcc atagaagaca ccgggaccga    660
tccagcctcc gcggccggga acggtgcatt ggaacgcgga ttccccgtgc caagagtgac    720
gtaagtaccg cctatagagt ctataggccc accccccttgg cttcttatgc atgctatact    780
gttttttggct tggggtctat acaccccgc ttcctcatgt tataggtgat ggtatagctt    840
agcctatagg tgtgggttat tgaccattat tgaccactcc cctattggtg acgatacttt    900
ccattactaa tccataacat ggctctttgc cacaactctc tttattggct atatgccaat    960
acactgtcct tcagagactg acacggactc tgtatttta caggatgggg tctcatttat    1020
tatttacaaa ttcacatata caacaccacc gtccccagtg cccgcagttt ttattaaaca    1080
taacgtggga tctccacgcg aatctcgggt acgtgttccg gacatgggct cttctccggt    1140
agcggcggag cttctacatc cgagccctgc tcccatgcct ccagcgactc atggtcgctc    1200
ggcagctcct tgctcctaac agtggaggcc agacttaggc acagcacgat gcccaccacc    1260
accagtgtgc cgcacaaggc cgtggcggta gggtatgtgt ctgaaaatga gctcggggag    1320
cgggcttgca ccgctgacgc atttggaaga cttaaggcag cggcagaaga agatgcaggc    1380
agctgagttg ttgtgttctg ataagagtca gaggtaactc ccgttgcggt gctgttaacg    1440
gtggagggca gtgtagtctg agcagtactc gttgctgccg cgcgcgccac cagacataat    1500
agctgacaga ctaacagact gttcctttcc atgggtcttt tctgcagtca ccgtccttga    1560
cacg                                                                  1564
```

<210> SEQ ID NO 23
<211> LENGTH: 3902
<212> TYPE: DNA
<213> ORGANISM: Artificial Sequence
<220> FEATURE:
<223> OTHER INFORMATION: pHP2

<400> SEQUENCE: 23

```
gactcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
gtatttacgg taaactgccc acttggcagt acatcaagtg tatcatatgc caagtacgcc    300
```

-continued

```
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc gtttagtgaa ccgtcagatc gcctggagac gccatccacg    660
ctgttttgac ctccatagaa gacaccggga ccgatccagc ctccgcggcc gggaacggtg    720
cattggaacg cggattcccc gtgccaagag tgacgtaagt accgcctata gagtctatag    780
gcccaccccc ttggcttctt atgcatgcta tactgttttt ggcttggggt ctatacaccc    840
ccgcttcctc atgttatagg tgatggtata gcttagccta taggtgtggg ttattgacca    900
ttattgacca ctcccctatt ggtgacgata ctttccatta ctaatccata acatggctct    960
ttgccacaac tctctttatt ggctatatgc caatacactg tccttcagag actgacacgg   1020
actctgtatt tttacaggat ggggtctcat ttattattta caaattcaca tatacaacac   1080
caccgtcccc agtgcccgca gtttttatta aacataacgt gggatctcca cgcgaatctc   1140
gggtacgtgt tccggacatg ggctcttctc cggtagcggc ggagcttcta catccgagcc   1200
ctgctcccat gcctccagcg actcatggtc gctcggcagc tccttgctcc taacagtgga   1260
ggccagactt aggcacagca cgatgcccac caccaccagt gtgccgcaca aggccgtggc   1320
ggtagggtat gtgtctgaaa atgagctcgg ggagcgggct tgcaccgctg acgcatttgg   1380
aagacttaag gcagcggcag aagaagatgc aggcagctga gttgttgtgt tctgataaga   1440
gtcagaggta actcccgttg cggtgctgtt aacggtggag ggcagtgtag tctgagcagt   1500
actcgttgct gccgcgcgcg ccaccagaca taatagctga cagactaaca gactgttcct   1560
ttccatgggt cttttctgca gtcaccgtcc ttgacacggc tagcgtttaa acttaagctt   1620
ggtaccgagc tcggatccac tagtccagtg tggtggaatt ctgcagatat ccagcacagt   1680
ggcggccgct cgagtctaga gggcccgttt aaacccgctg atcagcctcg actgtgcctt   1740
ctagttgcca gccatctgtt gtttgcccct ccccgtgcc ttccttgacc ctggaaggtg   1800
ccactcccac tgtcctttcc taataaaatg aggaaattgc atcgcattgt ctgagtaggt   1860
gtcattctat tctgggggt ggggtggggc aggacagcaa gggggaggat tgggaagaca   1920
atagcaggca tgctggggat gcggtgggct ctatggcttc tactgggcgg ttttatggac   1980
agcaagcgaa ccggaattgc cagctggggc gccctctggt aaggttggga agccctgcaa   2040
agtaaactgg atggctttct cgccgccaag gatctgatgg cgcaggggat caagctctga   2100
tcaagagaca ggatgaggat cgtttcgcat gattgaacaa gatggattgc acgcaggttc   2160
tccggccgct tgggtggaga ggctattcgg ctatgactgg gcacaacaga caatcggctg   2220
ctctgatgcc gccgtgttcc ggctgtcagc gcaggggcgc ccggttcttt ttgtcaagac   2280
cgacctgtcc ggtgccctga atgaactgca agacgaggca gcgcggctat cgtggctggc   2340
cacgacgggc gttccttgcg cagctgtgct cgacgttgtc actgaagcgg gaagggactg   2400
gctgctattg ggcgaagtgc cggggcagga tctcctgtca tctcaccttg ctcctgccga   2460
gaaagtatcc atcatggctg atgcaatgcg gcggctgcat acgcttgatc cggctacctg   2520
cccattcgac caccaagcga aacatcgcat cgagcgagca cgtactcgga tggaagccgg   2580
tcttgtcgat caggatgatc tggacgaaga gcatcagggg ctcgcgccag ccgaactgtt   2640
```

```
cgccaggctc aaggcgagca tgcccgacgg cgaggatctc gtcgtgaccc atggcgatgc    2700
ctgcttgccg aatatcatgg tggaaaatgg ccgcttttct ggattcatcg actgtggccg    2760
gctgggtgtg gcggaccgct atcaggacat agcgttggct acccgtgata ttgctgaaga    2820
gcttggcggc gaatgggctg accgcttcct cgtgctttac ggtatcgccg ctcccgattc    2880
gcagcgcatc gccttctatc gccttcttga cgagttcttc tgaattatta acgcttacaa    2940
tttcctgatg cggtattttc tccttacgca tctgtgcggt atttcacacc gcatacaggt    3000
ggcacttttc ggggaaatgt gcgcggaacc cctatttgtt tattttttcta aatacattca    3060 aatatgtatc cgctcatgag acaataaccc tgataaatgc ttcaataata gcacgtgcta    3120
aaacttcatt tttaatttaa aaggatctag gtgaagatcc ttttttgataa tctcatgacc    3180 aaaatccctt aacgtgagtt ttcgttccac tgagcgtcag accccgtaga aaagatcaaa    3240
ggatcttctt gagatccttt ttttctgcgc gtaatctgct gcttgcaaac aaaaaaacca    3300
ccgctaccag cggtggtttg tttgccggat caagagctac caactctttt tccgaaggta    3360
actggcttca gcagagcgca gataccaaat actgtccttc tagtgtagcc gtagttaggc    3420
caccacttca agaactctgt agcaccgcct acatacctcg ctctgctaat cctgttacca    3480
gtggctgctg ccagtggcga taagtcgtgt cttaccgggt tggactcaag acgatagtta    3540
ccggataagg cgcagcggtc gggctgaacg gggggttcgt gcacacagcc cagcttggag    3600
cgaacgacct acaccgaact gagatacctac agcgtgagc tatgagaaag cgccacgctt    3660
cccgaaggga gaaaggcgga caggtatccg gtaagcggca gggtcggaac aggagagcgc    3720
acgagggagc ttccagggg aaacgcctgg tatctttata gtcctgtcgg gtttcgccac    3780
ctctgacttg agcgtcgatt tttgtgatgc tcgtcagggg ggcggagcct atggaaaaac    3840
gccagcaacg cggcctttt acggttcctg gccttttgct ggccttttgc tcacatgttc    3900
tt                                                                   3902
```

<210> SEQ ID NO 24
<211> LENGTH: 1552
<212> TYPE: DNA
<213> ORGANISM: Artificial Sequence
<220> FEATURE:
<223> OTHER INFORMATION: 3157 strain (GQ221974) full HCMV IE

<400> SEQUENCE: 24

```
tgacattgat tattgactag ttattaatag taatcaatta cggggtcatt agttcatagc      60
ccatatatgg agttccgcgt tacataactt acggtaaatg gcccgcctgg ctgaccgccc     120
aacgaccccc gcctattgac gtcaataatg acgtagttc ccatagtaac gccaataggg     180
actttccatt gacgtcaatg ggtggagtat ttacggtaaa ctgcccactt ggcagtacat     240
caaatgtatc atatgccaag tacgccccct attgacgtca atgacggtaa atggcccgcc     300
tggcattatg cccagtacat gaccttacgg gactttccta cttggcagta catctacgta     360
ttagtcatcg ctattaccat ggtgatgcgg ttttggcagt acatcaatgg gcgtggatag     420
cggtttgact cacggggatt ccaagtctc caccccattg acgtcaatgg gagtttgttt     480
tggcaccaaa tcaacggga ctttccaaaa tgtcgtaata actccgcccc attgacgcaa     540
atgggcggta ggcgtgtact atgggaggtc tatataagca gagttcgttt agtgaaccgt     600
cagatcgcct ggagacgcca tccacgctgt tttgacctcc atagaagaca ccgggaccga     660
tccagcctcc gcggccggga acggtgcatt ggaacgcgga ttccccgtgc caagagtgac     720
gtaagtaccg cctatagact ctataggcac accccttgg ctcttatgca tgctatactg     780
```

-continued

```
tttttggctt gggcctata caccccgct tccttatgct ataggtgatg gtatagctta      840
gcctataggt gtgggttatt gaccattatt gaccactccc ctattggtga cgatactttc     900
cattactaat ccataacatg gctctttgcc acaactctct tgttggcta tatgccaata      960 ctgtcattca gagactgaca cggactctgt atttttacag gaaggggtcc catttattat    1020
ttacaaattc acatatataa caccgtcccc agtgcccgca gttttattta aacataacgt    1080
gggatctcca cgcgaatctc gggtacgtgt tccggacatg gctcttctc cggtagcggc     1140 ggagcttcca catccgagcc ctgctcccat gcctccagcg gctcatggtc gctcggcagc    1200
tccttgctcc taacagtgga ggccagactt aggcacagca cgatgcccac caccaccagt    1260
gtgccgcaca aggccgtggc ggtagggtat gtgtctgaaa atgagctcgg ggaatgggct    1320
tgcaccgctg acgcagatgg aagacttaag gcagcagcag aagaagcagg cagctgagtt    1380
gtgttctgtt gagagtcaga ggtaactcct gttgcggtgc tgttaacggt ggagggcagt    1440
gtagtctgag cagtactcgt tgctgccgcg cgcgccacca gacataatag ctgacagact    1500
aacagactgt tcctttccat ggatcctttc tgcagtcacc gtccttgaca cg            1552
```

<210> SEQ ID NO 25
<211> LENGTH: 3890
<212> TYPE: DNA
<213> ORGANISM: Artificial Sequence
<220> FEATURE:
<223> OTHER INFORMATION: pHP3

<400> SEQUENCE: 25

```
gactcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcctat tgacgtcaat    180
aatgacgtga gttcccatag taacgccaat agggactttc cattgacgtc aatgggtgga    240
gtatttacgg taaactgccc acttggcagt acatcaaatg tatcatatgc caagtacgcc    300
ccctattgac gtcaatgacg gtaaatggcc cgcctggcat tatgcccagt acatgacctt    360
acgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaattcaac gggactttcc    540
aaaatgtcgt aataactccg ccccattgac gcaaatgggc ggtaggcgtg tactatggga    600
ggtctatata agcagagttc gtttagtgaa ccgtcagatc gcctggagac gccatccacg    660
ctgttttgac ctccatagaa gacaccggga ccgatccagc ctccgcggcc gggaacggtg    720
cattggaacg cggattcccc gtgccaagag tgacgtaagt accgcctata gactctatag    780 gcacaccct ttggctctta tgcatgctat actgttttg gcttgggcc tatacacccc     840 cgcttcctta tgctataggt gatggtatag cttagcctat aggtgtgggt tattgaccat    900
tattgaccac tcccctattg gtgacgatac tttccattac taatccataa catggctctt    960
tgccacaact ctcttgttg gctatatgcc aatactgtca ttcagagact gacacggact   1020 ctgtatttt acaggaaggg gtcccattta ttatttacaa attcacatat ataacaccgt    1080
ccccagtgcc cgcagttttt attaaacata acgtgggatc tccacgcgaa tctcgggtac    1140
gtgttccgga catgggctct ctcggtag cggcggagct tccacatccg agccctgctc    1200
ccatgcctcc agcggctcat ggtcgctcgg cagctccttg ctcctaacag tggaggccag   1260
```

-continued

```
acttaggcac agcacgatgc ccaccaccac cagtgtgccg cacaaggccg tggcggtagg    1320
gtatgtgtct gaaaatgagc tcggggaatg ggcttgcacc gctgacgcag atggaagact    1380
taaggcagca gcagaagaag caggcagctg agttgtgttc tgttgagagt cagaggtaac    1440
tcctgttgcg gtgctgttaa cggtggaggg cagtgtagtc tgagcagtac tcgttgctgc    1500
cgcgcgcgcc accagacata atagctgaca gactaacaga ctgttccttt ccatggatcc    1560
tttctgcagt caccgtcctt gacacggcta gcgtttaaac ttaagcttgg taccgagctc    1620
ggatccacta gtccagtgtg gtggaattct gcagatatcc agcacagtgg cggccgctcg    1680
agtctagagg gcccgtttaa acccgctgat cagcctcgac tgtgccttct agttgccagc    1740
catctgttgt ttgcccctcc cccgtgcctt ccttgaccct ggaaggtgcc actcccactg    1800
tcctttccta ataaaatgag gaaattgcat cgcattgtct gagtaggtgt cattctattc    1860
tggggggtgg ggtggggcag gacagcaagg gggaggattg ggaagacaat agcaggcatg    1920
ctggggatgc ggtgggctct atggcttcta ctgggcggtt ttatggacag caagcgaacc    1980
ggaattgcca gctggggcgc cctctggtaa ggttgggaag ccctgcaaag taaactggat    2040
ggctttctcg ccgccaagga tctgatggcg caggggatca agctctgatc aagagacagg    2100
atgaggatcg tttcgcatga ttgaacaaga tggattgcac gcaggttctc cggccgcttg    2160
ggtggagagg ctattcggct atgactggga caacagaca atcggctgct ctgatgccgc    2220
cgtgttccgg ctgtcagcgc aggggcgccc ggttcttttt gtcaagaccg acctgtccgg    2280
tgccctgaat gaactgcaag acgaggcagc gcggctatcg tggctggcca cgacgggcgt    2340
tccttgcgca gctgtgctcg acgttgtcac tgaagcggga agggactggc tgctattggg    2400
cgaagtgccg gggcaggatc tcctgtcatc tcaccttgct cctgccgaga agtatccat     2460 catggctgat gcaatgcggc ggctgcatac gcttgatccg gctacctgcc cattcgacca    2520
ccaagcgaaa catcgcatcg agcgagcacg tactcggatg aagccggtc ttgtcgatca     2580 ggatgatctg gacgaagagc atcagggct cgcgccagcc gaactgttcg ccaggctcaa     2640
ggcgagcatg cccgacggcg aggatctcgt cgtgacccat ggcgatgcct gcttgccgaa    2700
tatcatggtg gaaaatggcc gcttttctgg attcatcgac tgtggccggc tgggtgtggc    2760
ggaccgctat caggacatag cgttggctac ccgtgatatt gctgaagagc ttggcggcga    2820
atgggctgac cgcttcctcg tgctttacgg tatcgccgct cccgattcgc agcgcatcgc    2880
cttctatcgc cttcttgacg agttcttctg aattattaac gcttacaatt tcctgatgcg    2940
gtattttctc cttacgcatc tgtgcggtat ttcacaccgc atacaggtgg cacttttcgg    3000
ggaaatgtgc gcggaacccc tatttgttta ttttttctaaa tacattcaaa tatgtatccg    3060
ctcatgagac aataaccctg ataaatgctt caataatagc acgtgctaaa acttcatttt    3120
taatttaaaa ggatctaggt gaagatcctt tttgataatc tcatgaccaa aatcccttaa    3180
cgtgagtttt cgttccactg agcgtcagac cccgtagaaa agatcaaagg atcttcttga    3240 gatcctttt ttctgcgcgt aatctgctgc ttgcaaacaa aaaaaccacc gctaccagcg     3300
gtggtttgtt tgccggatca agagctacca actctttttc cgaaggtaac tggcttcagc    3360
agagcgcaga taccaaatac tgtccttcta gtgtagccgt agttaggcca ccacttcaag    3420
aactctgtag caccgcctac atacctcgct ctgctaatcc tgttaccagt ggctgctgcc    3480
agtggcgata gtcgtgtct taccggggttg gactcaagac gatagttacc ggataaggcg    3540
cagcggtcgg gctgaacggg gggttcgtgc acacagccca gcttggagcg aacgacctac    3600
accgaactga gatacctaca gcgtgagcta tgagaaagcg ccacgcttcc cgaagggaga    3660
```

```
aaggcggaca ggtatccggt aagcggcagg tcggaacag gagagcgcac gagggagctt    3720 ccaggggaa acgcctggta tctttatagt cctgtcgggt ttcgccacct ctgacttgag    3780
cgtcgatttt tgtgatgctc gtcagggggg cggagcctat ggaaaaacgc cagcaacgcg    3840 gccttttac ggttcctggg cttttgctgg ccttttgctc acatgttctt                3890
```

<210> SEQ ID NO 26
<211> LENGTH: 1563
<212> TYPE: DNA
<213> ORGANISM: Artificial Sequence
<220> FEATURE:
<223> OTHER INFORMATION: CINCY+Towne fusion (GU980198.1) full HCMV IE

<400> SEQUENCE: 26

```
tgacattgat tattgactag ttatttataa taatcaatta cggggtcatt agttcatagc      60
ccatatatgg agttccgcgt tacataactt acggtaaatg gcccgcctgg ctgaccgccc     120
aacgaccccc gcccattgac gtcaataatg acgtgcgttc ccatagtaac gccaataggg     180
actttccatt gacgtcaatg ggtggagtat ttacggtaaa ctgcccactt ggcagtacat     240
caagtgtatc atatgccaag tccgcccccct attgacgtca atgacggtaa atggcccgcc    300
tggcattatg cccagtacat gaccttacgg gactttccta cttggcagta catctacgta     360
ttagtcatcg ctattaccat ggtgatgcgg ttttggcagt acaccaatgg gcgtggatag     420
cggtttgact cacggggatt tccaagtctc cacccccattg acgtcaatgg gagtttgttt     480
tggcaccaaa atcaacggga ctttccaaaa tgtcgtaata ctccgccccc gttgacgcaa     540
atgggcggta ggcgtgtacg ttgggaggtc tatataagca gagctcgttt agtgaaccgt     600
cagatcgcct ggagacgcca tccacgctgt tttgacctcc atagaagaca ccgggaccga     660
tccagcctcc gcggccggga acggtgcatt ggaacgcgga tttcccgtgc caagagtgac     720
gtaagtaccg cctatagact ctataggcac ccccctttgg ctcttatgca tgctatactg     780
tttttggctt ggggcctata caccccgct tccttatgct ataggtgatg gtatagctta     840
gcctataggt gtgggttatt gaccattatt gaccactccc ctattggtga caatactttc     900
cattactaat ccataacatg gctctttgcc acaactatct ttattggcta tatgccaata     960
ctctgtcctt cagagactga cacggactct gtattttac aggatggggt cccatttatt    1020
atttacaaat tcacatatac aacaacgccg tcccccgtgc ccgcagtttt tattaaacat    1080
agcgtgggat ctccacgcga atctcgggta cgtgttccgg acatgggctc ttctccggta    1140
gcggcggagc ttccacatcc gagccctggt cccatgcctc cagcggctca tggtcgctcg    1200
gcagctcctt gctcctaaca gtggaggcca gacttaggca cagcacaatg cccaccacca    1260
ccagtgtgcc gcacaaggcc gtggcggtag ggtatgtgtc tgaaaatgag ctcggagatt    1320
gggctcgcac cgctgacgca gatggaagac ttaaggcagc ggcagaagaa gatgcaggca    1380
gctgagttgt tgtattctga taagagtcag aggtaactcc cgttgcggtg ctgttaacgg    1440
tggagggcag tgtagtctga gcagtactcg ttgctgccgc gcgcgccacc agacataata    1500
gctgacagac taacagactg ttcctttcca tgggtctttt ctgcagtcac cgtccttgac    1560
acg                                                                  1563
```

<210> SEQ ID NO 27
<211> LENGTH: 3901
<212> TYPE: DNA
<213> ORGANISM: Artificial Sequence
<220> FEATURE:

<223> OTHER INFORMATION: pHP4

<400> SEQUENCE: 27

| | | | | | |
|---|---|---|---|---|---|
| gactcttcgc | gatgtacggg | ccagatatac | gcgttgacat | tgattattga | ctagttattt | 60 |
| ataataatca | attacggggt | cattagttca | tagcccatat | atggagttcc | gcgttacata | 120 |
| acttacggta | aatggcccgc | ctggctgacc | gcccaacgac | ccccgcccat | tgacgtcaat | 180 |
| aatgacgtgc | gttcccatag | taacgccaat | agggactttc | cattgacgtc | aatgggtgga | 240 |
| gtatttacgg | taaactgccc | acttggcagt | acatcaagtg | tatcatatgc | caagtccgcc | 300 |
| ccctattgac | gtcaatgacg | gtaaatggcc | cgcctggcat | tatgcccagt | acatgacctt | 360 |
| acgggacttt | cctacttggc | agtacatcta | cgtattagtc | atcgctatta | ccatggtgat | 420 |
| gcggttttgg | cagtacacca | atgggcgtgg | atagcggttt | gactcacggg | gatttccaag | 480 |
| tctccacccc | attgacgtca | atgggagttt | gttttggcac | caaaatcaac | gggactttcc | 540 |
| aaaatgtcgt | aataactccg | ccccgttgac | gcaaatgggc | ggtaggcgtg | tacgttggga | 600 |
| ggtctatata | agcagagctc | gtttagtgaa | ccgtcagatc | gcctggagac | gccatccacg | 660 |
| ctgttttgac | ctccatagaa | gacaccggga | ccgatccagc | ctccgcggcc | gggaacggtg | 720 |
| cattggaacg | cggattttcc | cgtgccaagag | tgacgtaagt | accgcctata | gactctatag | 780 |
| gcacacccct | ttggctctta | tgcatgctat | actgtttttg | gcttggggcc | tatacacccc | 840 |
| cgcttcctta | tgctataggt | gatggtatag | cttagcctat | aggtgtgggt | tattgaccat | 900 |
| tattgaccac | tcccctattg | gtgacaatac | tttccattac | taatccataa | catggctctt | 960 |
| tgccacaact | atctttattg | gctatatgcc | aatactctgt | ccttcagaga | ctgacacgga | 1020 |
| ctctgtattt | ttacaggatg | ggtcccatt | tattatttac | aaattcacat | atacaacaac | 1080 |
| gccgtccccc | gtgcccgcag | tttttattaa | acatagcgtg | ggatctccac | gcgaatctcg | 1140 |
| ggtacgtgtt | ccggacatgg | gctcttctcc | ggtagcggcg | gagcttccac | atccgagccc | 1200 |
| tggtcccatg | cctccagcgg | ctcatggtcg | ctcggcagct | ccttgctcct | aacagtggag | 1260 |
| gccagactta | ggcacagcac | aatgcccacc | accaccagtg | tgccgcacaa | ggccgtggcg | 1320 |
| gtagggtatg | tgtctgaaaa | tgagctcgga | gattgggctc | gcaccgctga | gcagatgga | 1380 |
| agacttaagg | cagcggcaga | agaagatgca | ggcagctgag | ttgttgtatt | ctgataagag | 1440 |
| tcagaggtaa | ctcccgttgc | ggtgctgtta | acggtggagg | gcagtgtagt | ctgagcagta | 1500 |
| ctcgttgctg | ccgcgcgcgc | caccagacat | aatagctgac | agactaacag | actgttcctt | 1560 |
| tccatgggtc | ttttctgcag | tcaccgtcct | tgacacggct | agcgtttaaa | cttaagcttg | 1620 |
| gtaccgagct | cggatccact | agtccagtgt | ggtggaattc | tgcagatatc | cagcacagtg | 1680 |
| gcggccgctc | gagtctagag | ggcccgttta | aacccgctga | tcagcctcga | ctgtgccttc | 1740 |
| tagttgccag | ccatctgttg | tttgcccctc | ccccgtgcct | tccttgaccc | tggaaggtgc | 1800 |
| cactcccact | gtcctttcct | aataaaatga | ggaaattgca | tcgcattgtc | tgagtaggtg | 1860 |
| tcattctatt | ctggggggtg | gggtggggca | ggacagcaag | ggggaggatt | gggaagacaa | 1920 |
| tagcaggcat | gctggggatg | cggtgggctc | tatggcttct | actgggcggt | tttatggaca | 1980 |
| gcaagcgaac | cggaattgcc | agctggggcg | ccctctggta | aggttgggaa | gccctgcaaa | 2040 |
| gtaaactgga | tggctttctc | gccgccaagg | atctgatggc | gcagggatc | aagctctgat | 2100 |
| caagagacag | gatgaggatc | gtttcgcatg | attgaacaag | atggattgca | cgcaggttct | 2160 |
| ccggccgctt | gggtggagag | gctattcggc | tatgactggg | cacaacagac | aatcggctgc | 2220 |
| tctgatgccg | ccgtgttccg | gctgtcagcg | caggggcgcc | cggttctttt | tgtcaagacc | 2280 |

```
gacctgtccg gtgccctgaa tgaactgcaa gacgaggcag cgcggctatc gtggctggcc    2340
acgacgggcg ttccttgcgc agctgtgctc gacgttgtca ctgaagcggg aagggactgg    2400
ctgctattgg gcgaagtgcc ggggcaggat ctcctgtcat ctcaccttgc tcctgccgag    2460
aaagtatcca tcatggctga tgcaatgcgg cggctgcata cgcttgatcc ggctacctgc    2520
ccattcgacc accaagcgaa acatcgcatc gagcgagcac gtactcggat ggaagccggt    2580
cttgtcgatc aggatgatct ggacgaagag catcaggggc tcgcgccagc cgaactgttc    2640
gccaggctca aggcgagcat gcccgacggc gaggatctcg tcgtgaccca tggcgatgcc    2700
tgcttgccga atatcatggt ggaaaatggc cgcttttctg gattcatcga ctgtggccgg    2760
ctgggtgtgg cggaccgcta tcaggacata gcgttggcta cccgtgatat tgctgaagag    2820
cttggcggcg aatgggctga ccgcttcctc gtgctttacg gtatcgccgc tcccgattcg    2880
cagcgcatcg ccttctatcg ccttcttgac gagttcttct gaattattaa cgcttacaat    2940
ttcctgatgc ggtattttct ccttacgcat ctgtgcggta tttcacaccg catacaggtg    3000
gcacttttcg gggaaatgtg cgcggaaccc ctatttgttt attttctaa atacattcaa     3060 atatgtatcc gctcatgaga caataaccct gataaatgct tcaataatag cacgtgctaa    3120
aacttcattt ttaatttaaa aggatctagg tgaagatcct ttttgataat ctcatgacca    3180
aaatccctta acgtgagttt tcgttccact gagcgtcaga ccccgtagaa aagatcaaag    3240
gatcttcttg agatcctttt tttctgcgcg taatctgctg cttgcaaaca aaaaaaccac    3300
cgctaccagc ggtggtttgt ttgccggatc aagagctacc aactcttttt ccgaaggtaa    3360
ctggcttcag cagagcgcag ataccaaata ctgtccttct agtgtagccg tagttaggcc    3420
accacttcaa gaactctgta gcaccgccta catacctcgc tctgctaatc ctgttaccag    3480
tggctgctgc cagtggcgat aagtcgtgtc ttaccgggtt ggactcaaga cgatagttac    3540
cggataaggc gcagcggtcg ggctgaacgg ggggttcgtg cacacagccc agcttggagc    3600
gaacgaccta caccgaactg agatacctac agcgtgagct atgagaaagc gccacgcttc    3660
ccgaagggag aaaggcggac aggtatccgg taagcggcag ggtcggaaca ggagagcgca    3720
cgagggagct tccaggggga aacgcctggt atctttatag tcctgtcggg tttcgccacc    3780
tctgacttga gcgtcgattt ttgtgatgct cgtcaggggg gcggagccta tggaaaaacg    3840
ccagcaacgc ggccttttta cggttcctgg cttttgctg cctttttgct cacatgttct     3900
t                                                                    3901

<210> SEQ ID NO 28
<211> LENGTH: 795
<212> TYPE: DNA
<213> ORGANISM: Artificial Sequence
<220> FEATURE:
<223> OTHER INFORMATION: Kanamycin Resistance Gene

<400> SEQUENCE: 28
atgattgaac aagatggatt gcacgcaggt tctccggccg cttgggtgga gaggctattc      60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
caagacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
```

```
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgag catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795

<210> SEQ ID NO 29
<211> LENGTH: 477
<212> TYPE: DNA
<213> ORGANISM: Artificial Sequence
<220> FEATURE:
<223> OTHER INFORMATION: hGH pA

<400> SEQUENCE: 29
gggtggcatc cctgtgaccc ctccccagtg cctctcctgg ccctggaagt tgccactcca     60
gtgcccacca gccttgtcct aataaaatta gttgcatca ttttgtctga ctaggtgtcc    120
ttctataata ttatggggtg gagggggtg gtatggagca aggggcaagt tgggaagaca    180
acctgtaggg cctgcgggt ctattgggaa ccaagctgga gtgcagtggc acaatcttgg    240
ctcactgcaa tctccgcctc ctgggttcaa gcgattctcc tgcctcagcc tcccgagttg    300
ttgggattcc aggcatgcat gaccaggctc agctaatttt tgttttttg gtagagacgg    360 ggtttcacca tattggccag gctggtctcc aactcctaat ctcaggtgat ctacccacct    420
tggcctccca aattgctggg attacaggcg tgaaccactg ctcccttccc tgtcctt      477

<210> SEQ ID NO 30
<211> LENGTH: 225
<212> TYPE: DNA
<213> ORGANISM: Artificial Sequence
<220> FEATURE:
<223> OTHER INFORMATION: bGH pA

<400> SEQUENCE: 30
ctgtgccttc tagttgccag ccatctgttg tttgccccctc cccgtgcct tccttgaccc     60 tggaaggtgc cactcccact gtcctttcct aataaaatga ggaaattgca tcgcattgtc    120
tgagtaggtg tcattctatt ctggggggtg ggtggggca ggacagcaag ggggaggatt    180
gggaagacaa tagcaggcat gctggggatg cggtgggctc tatgg                  225

<210> SEQ ID NO 31
<211> LENGTH: 122
<212> TYPE: DNA
<213> ORGANISM: Artificial Sequence
<220> FEATURE:
<223> OTHER INFORMATION: SV40 early pA

<400> SEQUENCE: 31
aacttgttta ttgcagctta taatggttac aaataaagca atagcatcac aaatttcaca     60
aataaagcat ttttttcact gcattctagt tgtggtttgt ccaaactcat caatgtatct    120
ta                                                                  122

<210> SEQ ID NO 32
<211> LENGTH: 134
```

```
<212> TYPE: DNA
<213> ORGANISM: Artificial Sequence
<220> FEATURE:
<223> OTHER INFORMATION: SV40 late pA

<400> SEQUENCE: 32
atgctttatt tgtgaaattt gtgatgctat tgctttattt gtaaccatta taagctgcaa        60
taaacaagtt aacaacaaca attgcattca ttttatgttt caggttcagg gggaggtgtg       120
ggaggttttt taaa                                                         134
```